United States Patent

Bonutti

[11] Patent Number: 5,814,072
[45] Date of Patent: Sep. 29, 1998

[54] METHOD AND APPARATUS FOR USE IN ANCHORING A SUTURE

[76] Inventor: Peter M. Bonutti, 1303 W. Evergreen Plz., Effingham, Ill. 62401

[21] Appl. No.: 752,005

[22] Filed: Nov. 15, 1996

[51] Int. Cl.[6] .................................................. A61B 17/04
[52] U.S. Cl. ........................................ 606/232; 606/104
[58] Field of Search ........................... 606/72, 104, 103, 606/232, 898

[56] References Cited

U.S. PATENT DOCUMENTS

| | | |
|---|---|---|
| 4,235,238 | 11/1980 | Oglu et al. . |
| 4,448,194 | 5/1984 | DiGiovanni et al. . |
| 4,741,330 | 5/1988 | Hayhurst . |
| 5,002,550 | 3/1991 | Li . |
| 5,041,129 | 8/1991 | Hayhurst et al. . |
| 5,100,417 | 3/1992 | Cerier et al. . |
| 5,354,298 | 10/1994 | Lee et al. . |
| 5,403,348 | 4/1995 | Bonutti ................................ 606/232 |
| 5,464,426 | 11/1995 | Bonutti ................................ 606/232 |
| 5,549,630 | 8/1996 | Bonutti ................................ 606/232 |

*Primary Examiner*—Gary Jackson
*Attorney, Agent, or Firm*—Tarolli, Sundheim, Covell, Tummino & Szabo

[57] ABSTRACT

A suture anchor inserter includes a manually engageable handle and a shaft which extends from the handle through a passage in the anchor. During insertion of the anchor into body tissue, an end portion of the shaft pierces the body tissue in advance of the anchor. At the same time, a pusher surface on the shaft applies force against a trailing end portion of the anchor to push the anchor into the body tissue. The shaft may be formed as one piece or may include an inner member which is enclosed by an outer member which is movable relative to the inner member. During insertion of the anchor into body tissue, it may be desired to change the orientation of the anchor relative to the body tissue and the shaft of the inserter. When the orientation of the anchor is to be changed, rotational force is applied to the anchor by tensioning the suture and pressing the end portion of the shaft against an inner surface of the passage in the anchor.

129 Claims, 4 Drawing Sheets

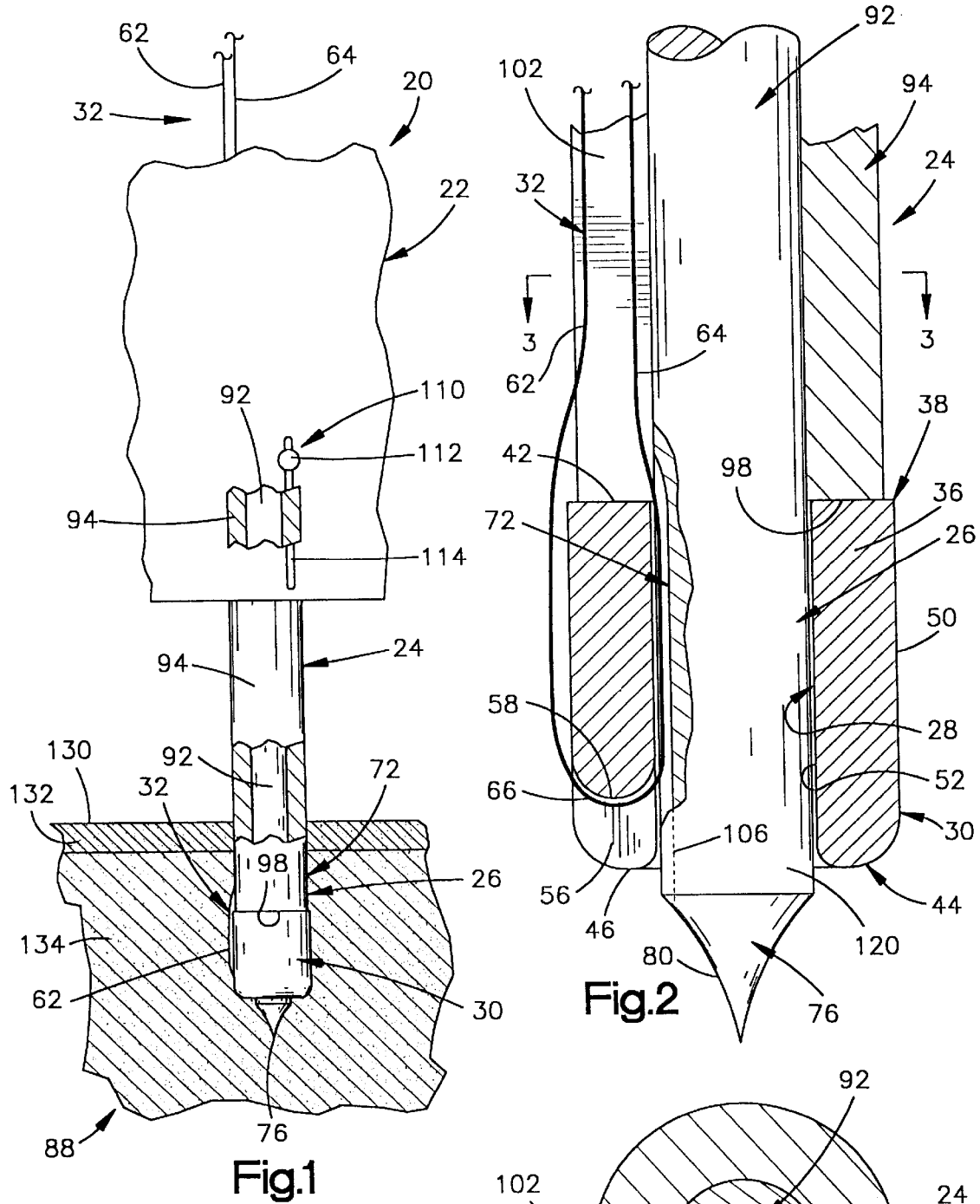
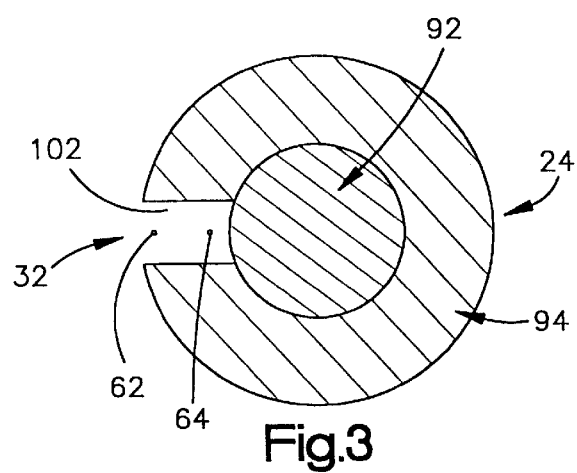

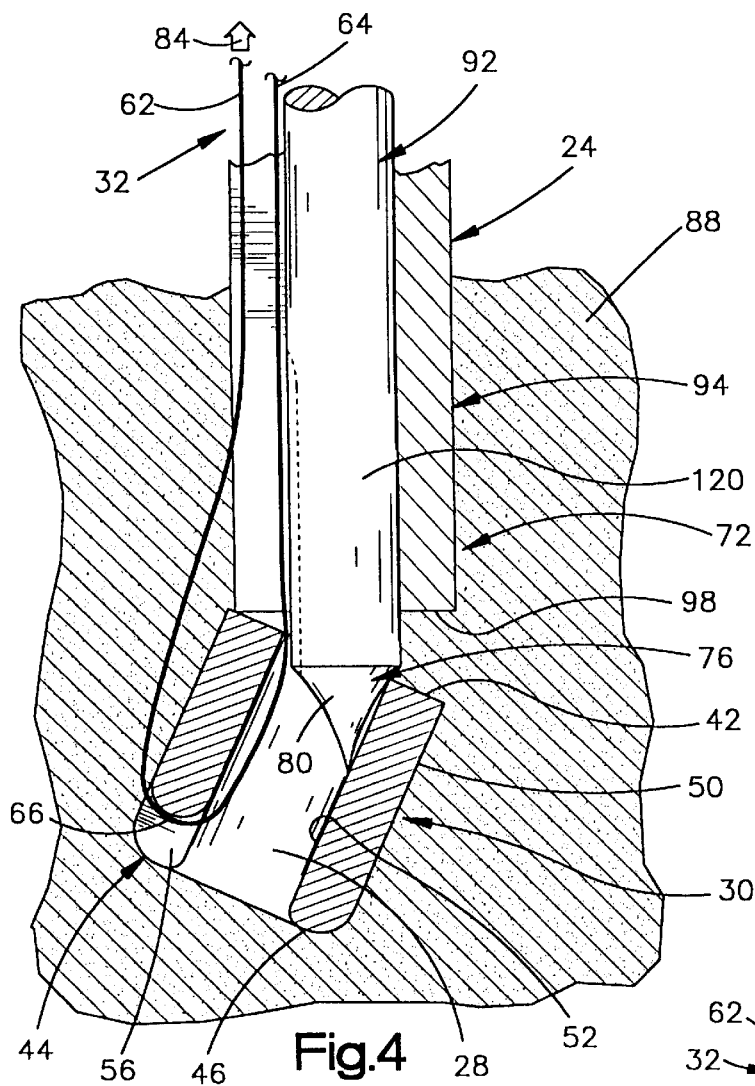
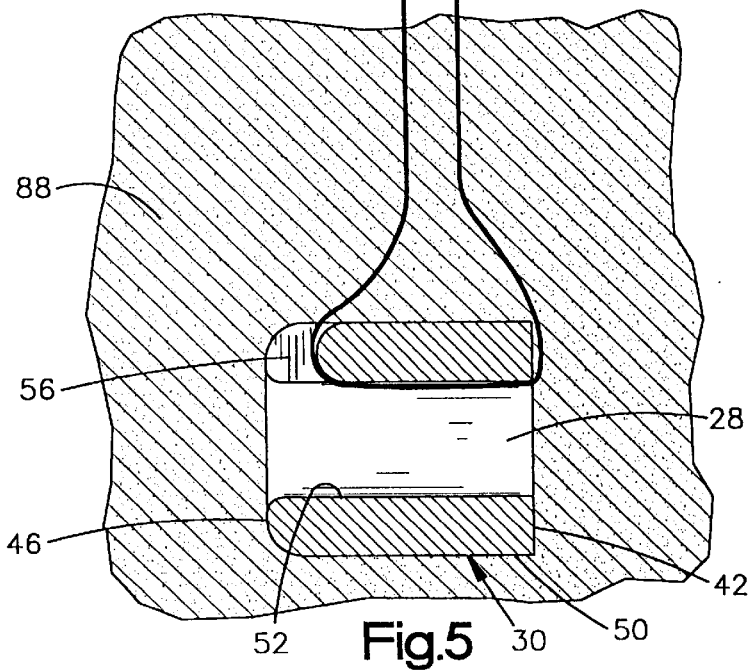

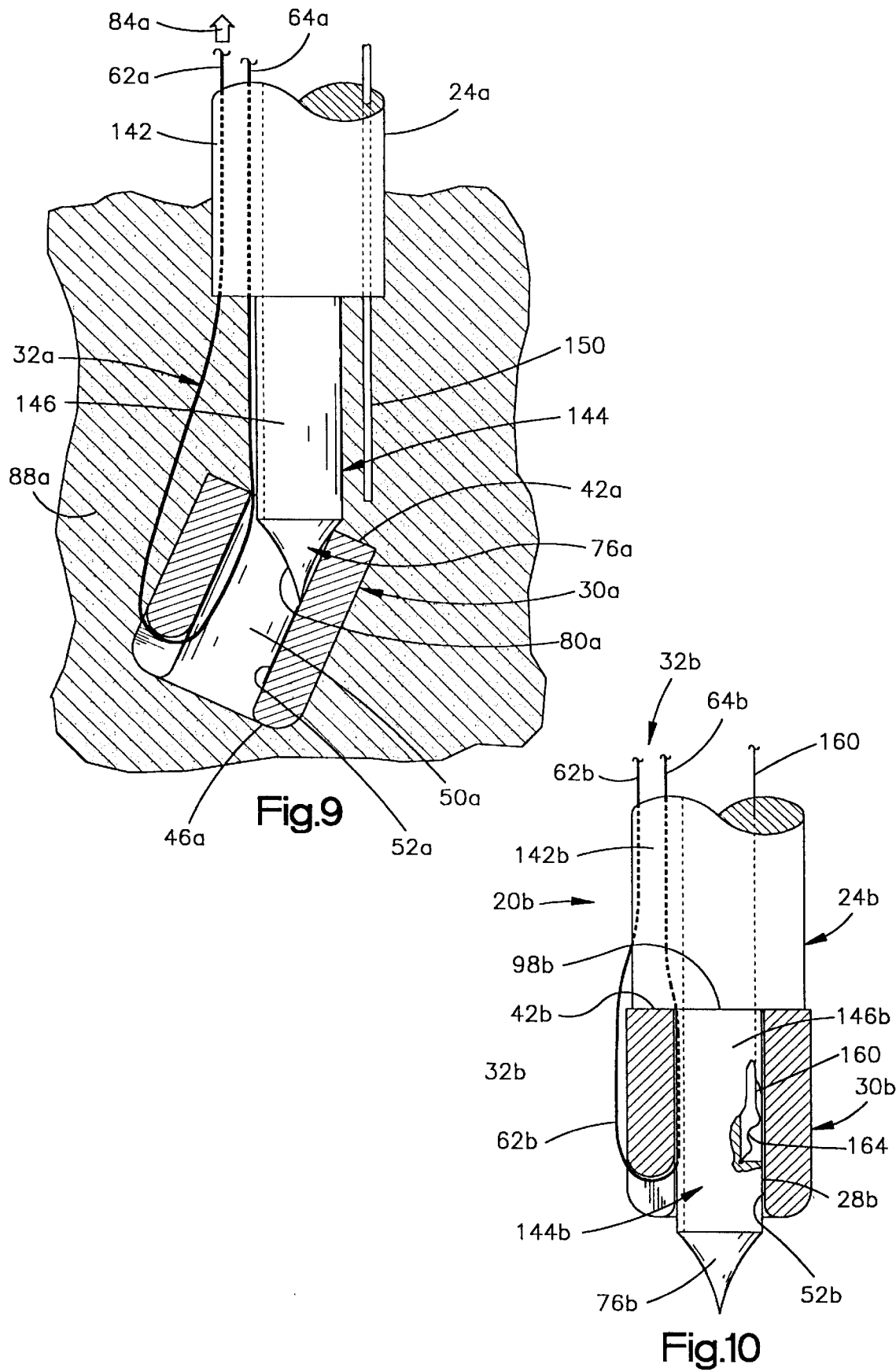

METHOD AND APPARATUS FOR USE IN ANCHORING A SUTURE

BACKGROUND OF THE INVENTION

The present invention relates to a new and improved suture anchor inserter and a method of using the suture anchor inserter to position a suture anchor in either soft or hard body tissue.

Surgeons utilize suture anchor inserters to position suture anchors in either soft body tissue or hard body tissue. Suture anchor inserters for positioning suture anchors in soft or hard body tissue are disclosed in U.S. Pat. Nos. 5,403,348; 5,464,426; and 5,549,630. During positioning of a suture anchor relative to body tissue, it may be necessary to form an opening in the body tissue to receive the anchor. Once the anchor has been received in the opening in body tissue, it may be desired to change the orientation of the anchor relative to the body tissue by pivoting or otherwise moving the anchor relative to body tissue.

SUMMARY OF THE INVENTION

The present invention relates to a new and improved suture anchor inserter and method of using the suture anchor inserter. The suture anchor inserter includes a handle and a shaft which extends outward from the handle. The shaft has a leading end portion which extends into an anchor. The leading end portion of the shaft may extend through the anchor and be pointed to facilitate piercing of body tissue by the leading end portion of the shaft.

Once the anchor has been inserted into the body tissue, it may be desired to change the orientation of the anchor relative to the body tissue. The orientation of the anchor relative to the body tissue may be changed by applying force against an inner side surface of the anchor with the leading end portion of the shaft. In one embodiment of the inserter, a portion of the shaft is movable relative to another portion of the shaft to facilitate separation of the anchor and shaft. In another embodiment of the inserter, the shaft is formed as one piece. A spring may advantageously be utilized to hold the anchor on the leading end portion of the shaft.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is a simplified schematic illustration of the manner in which an inserter constructed in accordance with the present invention may be utilized to insert an anchor into body tissue;

FIG. 2 is an enlarged fragmentary sectional view further illustrating the relationship between the anchor and a shaft of the inserter of FIG. 1;

FIG. 3 is a sectional view, taken generally along the line 3—3 of FIG. 2, illustrating the construction of the shaft of the inserter;

FIG. 4 is a schematic illustration depicting the manner in which the orientation of an anchor may be changed in the body tissue of FIG. 1 with the inserter;

FIG. 5 is a schematic illustration depicting the anchor of FIG. 4 after the anchor has been moved to a desired orientation in the body tissue;

FIG. 9 is a schematic illustration depicting the manner in which the orientation of an anchor may be changed in the body tissue of FIG. 6 with the inserter of FIGS. 6–8; and FIG. 10 is a schematic illustration depicting the relationship between a leading end portion of a shaft of a third embodiment of the inserter and an anchor.

DESCRIPTION OF SPECIFIC PREFERRED EMBODIMENTS OF THE INVENTION

General Description

Figures 6, 7:
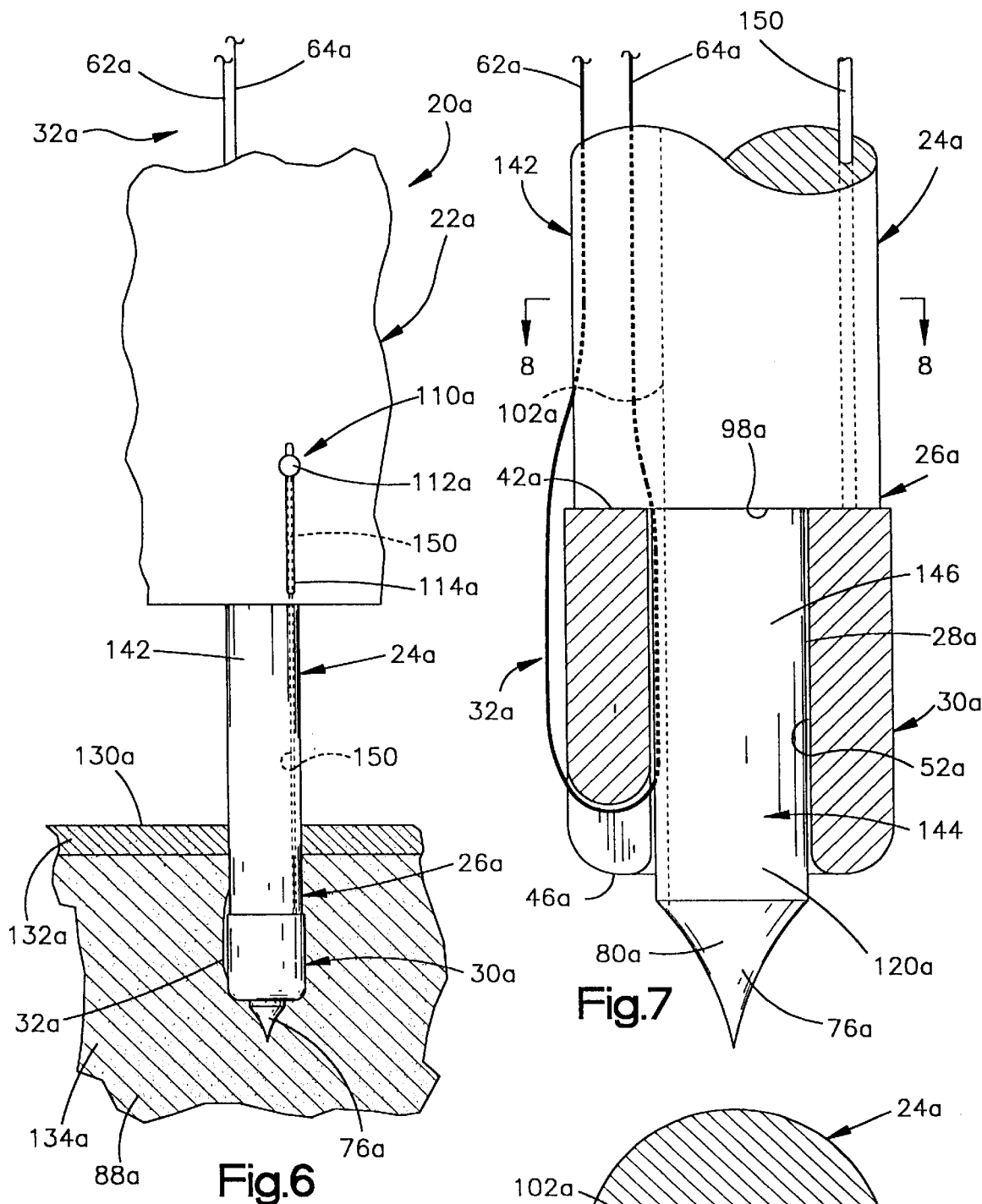
FIG. 6 is a schematic illustration, generally similar to FIG. 1, illustrating a second embodiment of the inserter.
FIG. 7 is an enlarged fragmentary sectional view illustrating the relationship between an anchor and a one-piece shaft of the inserter of FIG. 6.

A suture anchor inserter 20 constructed and used in accordance with the present invention is illustrated in FIG. 1. The suture anchor inserter 20 includes a manually engageable handle 22 and a shaft 24 which extends from the handle. A leading end portion 26 (FIG. 2) of the inserter 20 extends through a passage 28 in a suture anchor 30. A suture 32 engages the anchor 30.

The illustrated anchor 30 has a cylindrical tubular side wall 36 (FIG. 2). A trailing end portion 38 of the anchor 30 has a flat annular trailing end surface 42. In addition, the anchor 30 has a leading end portion 44. The leading end portion 44 of the anchor 30 has an annular leading end surface 46.

The tubular side wall 36 of the anchor 30 has a cylindrical outer side surface 50 which extends between the trailing end surface 42 and the leading end surface 46. In addition, the illustrated anchor 30 has a cylindrical inner side surface 52 which is disposed in a coaxial relationship with the outer side surface 50. The cylindrical inner side surface 52 forms the passage 28 which extends between the trailing end surface 42 and leading end surface 46 of the anchor 30.

A groove or slot 56 is formed in the leading end portion 44 of the anchor 30. The groove or slot 56 extends axially inward from the leading end surface 46 and extends radially between the outer and inner side surfaces 50 and 52 of the anchor 30. The slot or groove 56 has an arcuately curving inner side surface 58 across which the suture 32 extends. It is contemplated that the slot or groove 56 may be omitted if desired.

The suture 32 has an outer leg 62 which extends along the outer side surface 50 of the anchor 30. An inner leg 64 of the suture 32 extends through the passage 28 and along the inner side surface 52 of the anchor 30. The outer leg 62 and inner leg 64 of the suture 32 are interconnected by a connector section 66 of the suture. The connector section 66 of the suture 32 extends through the slot 56 in the side wall 36 of the anchor 30. If the anchor 30 is constructed without the slot 56, the connector section 66 of the suture 32 would extend across the leading end surface 46 of the anchor.

The anchor 30 is made of a biocompatible material, specifically, stainless steel. The anchor 30 has a length, that is, the distance between the trailing end surface 42 and leading end surface 46, of approximately two millimeters. The anchor 30 has an outside diameter, that is, the diameter of the outer side surface 50, of approximately one millimeter. The inner side surface 52 has a diameter of about one-half millimeter. It should be understood that the foregoing specific dimensions for one specific anchor 30 have been set forth herein only for purposes of clarity of description. It is contemplated that the anchor 30 will be constructed with dimensions which are different than the dimensions set forth above.

The illustrated anchor 30 has a cylindrical tubular side wall 36. It should be understood that the anchor 30 could have a different configuration. For example, the anchor 30 could have a polygonal cross sectional configuration if desired. Thus, the anchor 30 could have a polygonal configuration which is similar to the polygonal configuration of an anchor disclosed in U.S. Pat. No. 5,549,630 issued Sep. 27, 1996 to Peter M. Bonutti.

Although the anchor 30 is formed of metal, it is contemplated that the anchor 30 could be formed of other materials if desired. For example, the anchor 30 could be formed of body tissue. Alternatively, the anchor 30 could be formed of a polymeric material such as cellulose, petroylglutamic acid, collagen, or polylactide. It is believed that a ceramic as found in hydroxyapatite composites with polyethylene, polylactide or polyhydroxybutyrate may be utilized to form the anchor 30. If desired, the anchor 30 may be formed of a material which is hydrophilic and expands when exposed to body fluids.

In accordance with a feature of the present invention, the shaft 24 has a leading end portion 72 (FIGS. 1 and 2) which is used to penetrate human body tissue. The leading end portion 72 of the shaft extends through the anchor 30. The leading end portion 72 of the shaft 24 may have a point 76 which extends ahead of the leading end surface 46 of the anchor 30.

The illustrated point 76 on the inserter shaft 24 has a conical configuration with a central axis which is coincident with a central axis of the inserter shaft and anchor 30. However, if desired, the point 76 could have a wedge-shaped configuration. Similarly, the point 76 could be formed by a single flat plane which is skewed at an acute angle to a longitudinal central axis of the shaft 24. Alternatively, the leading end of the shaft 24 could have a rounded or even a flat configuration.

The leading end portion 72 of the shaft 24 extends through the passage 28 in the anchor 30. The point 76 on the leading end of the shaft 24 is disposed ahead of and is coaxial with the anchor 30. This enables the point 76 to pierce body tissue ahead of the anchor 30. Although it is believed that the provision of the point 76 on the leading end of the shaft 24 will facilitate the piercing of human body tissue, the cross sectional size of the leading end of the shaft may be so small as to enable the shaft to pierce body tissue with a blunt end.

By piercing the body tissue with the point 76, an opening is initially formed by the leading end portion 72 of the shaft 24. The shaft 24 moves the anchor into the opening which was initially formed by the point 76. The leading end surface 46 on the anchor 30 is sloped to form a continuation of a surface 80 on the point 76. The sloping leading end surface 46 on the anchor 30 promotes a smooth enlargement of the opening formed in the elastic material of the human body tissue by the point 76 on the leading end of the shaft 24. Although the point 76 is advantageously used to pierce soft body tissue, the inserter 20 may be used to position anchors 30 in preformed openings in hard body tissue, such as bone.

In accordance with another feature of the invention, the shaft 24 may be used to promote movement of the anchor 30 in human body tissue in such a manner as to change the orientation of the anchor relative to the body tissue and the shaft 24. Thus, it may be desired to change the orientation of the anchor 30 relative to the shaft 24 from the orientation shown in FIG. 1 to the orientation shown in FIG. 5. However, it should be understood that the inserter 20 may also be used to position suture anchors 30 which remain in the orientation shown in FIG. 1 relative to the body tissue.

When it is desired to change the orientation of an anchor 30 relative to body tissue, a leg 62 of the suture 32 is tensioned in the manner indicated by an arrow 84 in FIG. 4. At the same time, the point 76 on the shaft 24 engages the inner side surface 52 of the passage 28 through the anchor 30. This results in the application of a torque to the anchor 30 tending to rotate the anchor in a clockwise direction (as viewed in FIG. 4) from the orientation shown in FIG. 1 through the orientation shown in FIG. 4, toward the orientation shown in FIG. 5.

As this occurs, the cylindrical outer side surface 50 of the anchor is pressed against the elastic material of human body tissue 88 and deforms the body tissue. Once the anchor has been moved to the orientation shown in FIG. 5, pulling out of the anchor from the body tissue 88 is resisted by the relatively large outer side surface 50 of the anchor. This enables the anchor to remain stable in the body tissue 88 even though relatively large forces are applied to the legs 62 and 64 of the suture 32. Although the foregoing description has related to the changing of the orientation of the anchor 30 in soft body tissue, the inserter 20 may be used to change the orientation of an anchor in cancellous bone tissue in the same manner as previously set forth in association with soft body tissue.

Inserter

The suture anchor inserter 20 (FIG. 1) includes a handle 22 having a configuration suitable for manual grasping by a surgeon. The illustrated handle 22 has a generally cylindrical configuration with circumferentially extending grooves to facilitate firm gripping of the handle. However, if desired, the handle 22 could be formed with a generally triangular cross sectional configuration in a manner similar to that disclosed in U.S. application Ser. No. 08/673,923 filed Jul. 1, 1996 and entitled "Suture Anchor Inserter Assembly and Method" by Peter M. Bonutti.

The shaft 24 extends axially outward from the handle 22. The shaft 24 has a generally cylindrical configuration and is disposed in a coaxial relationship with the handle 22. However, the shaft 24 could have a different configuration if desired. For example, if the passage 28 through the anchor 30 had a polygonal cross sectional configuration, the shaft 24 could have a corresponding polygonal cross sectional configuration.

In accordance with a feature of the embodiment of the inserter 20 illustrated in FIGS. 1–3, the shaft 24 includes a cylindrical inner member 92 and cylindrical outer member 94 which are movable relative to each other. The upper (as viewed in FIGS. 1 and 2) end of the solid cylindrical inner member 92 is fixedly connected with the handle 22. The point 76 is disposed on the lower (as viewed in FIGS. 1 and 2) end of the inner member 92. The point 76 extends ahead of the leading end portion 44 of the anchor 30 to initiate formation of an opening into which the anchor moves.

As was previously mentioned, the point 76 could be formed with a configuration other than the illustrated conical configuration. In fact, it is contemplated that the point 76 may be eliminated on some embodiments of the inserter. Although it is preferred to have the inner member 92 extend through the passage 28 and extend ahead of the leading end portion 44 of the anchor 30, the leading end of the inner member 92 could be disposed in the anchor if desired.

The outer member 94 has a tubular cylindrical configuration and partially encloses the solid inner member 92. The outer member 94 is axially movable relative to the inner member 92. The outer member 94 has a flat annular pusher surface 98 which engages the flat annular trailing end surface 42 of the anchor 30.

The inner and outer members 92 and 94 are both formed of metal, specifically stainless steel. However, the inner and outer members 92 and 94 could be formed of other materials if desired. For example, the inner member 92 could be formed of metal and the outer member 94 could be formed of a polymeric material.

The outer member 94 is axially movable along the inner member 92 between a retracted position, shown in FIGS. 1 and 2, and a fully extended position in which the pusher surface 98 is adjacent to the lower (as viewed in FIG. 2) end of the point 76. Thus, the outer member 94 is movable axially along the inner member 92 from the position shown in FIGS. 1 and 2 through the position shown in FIG. 4 to a position in which the annular pusher surface 98 is a short distance past the outer end of the point 76.

A slot or groove 102 (FIG. 3) extends through a tubular cylindrical side wall of the outer member 94. The straight slot or groove 102 in the outer member 94 extends between opposite ends of the outer member 94 and is axially aligned with a passage which extends through the handle 22. The two legs 62 and 64 of the suture 32 extend through the slot 102 and the passage in the handle 22 to a location disposed above (as viewed in FIG. 1) the handle.

The inner leg 64 of the suture 32 extends through the passage 28 (FIG. 2) in the anchor 30. The leading end portion of the inner member 92 also extends through the passage 28 in the anchor 30. In the illustrated embodiment of the inserter 20, a straight slot or groove 106 extends axially along the inner member 92 from the point 76 to a location which is disposed above (as viewed in FIG. 2), the pusher surface 98 when the outer member 94 is in the retracted position. The inner leg 64 of the suture then extends from the slot 106 in the inner member 92 into the slot 102 in the outer member 94. The slot 106 in the inner member 92 terminates at a location disposed axially above (as viewed in FIG. 2) the pusher surface 98 when the pusher surface is in the retracted position.

An actuator 110 is provided to move the outer member 94 axially along the inner member 92. The actuator 110 (FIG. 1) includes a manually engageable knob or input member 112 which is connected to the outer member 94 and extends through a slot 114 formed in the handle 22. The slot 114 has an axial extent which corresponds to the distance which the outer member 94 can be moved axially along the inner member 92. When the outer member 94 is in the fully retracted position of FIG. 1, the knob 112 is adjacent to an upper end of the slot 114.

After the anchor 30 has been moved into body tissue 88 and is to remain in the orientation shown in FIG. 1, the actuator knob 112 is moved downward (as viewed in FIG. 1) in the slot 114. As this occurs, force is transmitted between the pusher surface 98 and the trailing end surface 42 of the anchor 30. At the same time, the shaft 24 may be moved straight upward (as viewed in FIG. 1).

The relative movement between the anchor 30 and inner member 92 results in the trailing end surface 42 of the anchor 30 being moved in alignment with the base or upper end of the point 76. When this has happened, a cylindrical outer side or positioning surface 120 on the inner member 92 is disposed above (as viewed in FIG. 2) the annular trailing end surface 42 of the anchor 30. Continued relative movement between the inner and outer members 92 and 94 at least partially withdraws the point 76 from the passage 28 in the anchor 30. The handle 22 of the inserter 20 can then be moved or pulled upward away from the body tissue 88 and the point 76 of the shaft 24 moved completely out of the anchor 30. This results in the anchor 30 remaining in the orientation shown in FIG. 1 in the body tissue 88.

As the outer member 94 is moved axially downward (as viewed in FIGS. 1 and 2) to separate the anchor from the shaft 24, the extent of the telescopic relationship between the portions of the inner and outer members 92 and 94 disposed in the handle 22 is decreased. Thus, when the outer member 94 is in the fully retracted position shown in FIG. 1, the extent to which the portion of the inner member 92 disposed in the handle is enclosed by the outer member 94 is a maximum. As the actuator knob 112 is moved downward (as viewed in FIG. 1) in the slot 114, a portion of the outer member 94 moves out of the handle 22 and the extent of the telescopic relationship between the inner and outer members 92 and 94 in the handle 22 decreases.

The length of the slot 114 is great enough to enable the pusher surface 98 to move along the length of the point 76. When the actuator knob 112 has reached the lower end (as viewed in FIG. 1) of the slot 114, the upper end portion of the outer member 94 is still in the handle 22. At this time, the pusher surface 98 has moved to a location just past the point 76. Therefore, the point 76 is fully enclosed by the outer member 94.

It should be understood that a surgeon using the inserter 20 can determine the extent of relative movement between the inner and outer members 92 and 94. The surgeon may move the actuator knob 112 through only a portion of the length of the slot 114. Suitable indicia may be provided along the slot 114 to indicate the position of the pusher surface 98 relative to the point 76.

In the embodiment of the invention illustrated in FIG. 1, the actuator knob 112 is connected directly with the outer member 94 and is movable in the slot 114 in the handle 22. However, it is contemplated that the actuator knob 112 and the slot 114 could be eliminated and suitable knurling and/or projections provided on the outer member 94. The knurling or projections on the outer member 94 may be manually engaged and force transmitted directly from the hand of a surgeon to the outer member. If force is to be manually applied directly to the outer member 94, the outer member could either extend into the handle 22 or terminate short of the handle.

Insertion of Anchor

When the anchor 30 is to be inserted into body tissue 88, the suture 32 extends through the passage 28 in the anchor 30. The legs 62 and 64 of the suture 32 extend along the slot 102 in the outer member 94 and through the passage (not shown) in the handle 22. However, if desired, the legs 62 and 64 of the suture 32 could extend along the outside of the shaft 24 and handle 22.

The anchor 30 is then positioned on the leading end portion 26 of the inserter 20 with the suture 32 extending through the passage 28 in the anchor and with the outer member 94 in the retracted position of FIGS. 1 and 2. It should be understood that the suture 32 could be connected with the anchor 30 in a manner other than by extending through the passage 28. For example, an opening could be provided in the anchor 30 at a location spaced from the passage 28. The suture 32 could extend through or be tied off at this opening.

To position the anchor 30 on the leading end portion 26 of the shaft 24, the point 76 on the inner member 92 is inserted into the passage 28 in the anchor 30. The slot 106 in the inner member 92 is aligned with the inner leg 64 of the suture. The anchor is then moved along the inner member 92 until the trailing end surface 42 on the anchor moves into abutting engagement with the pusher surface 98 on the outer member 94. At this time, the point 76 on the inner member 92 extends outward from and is coaxial with the end surface 46 of the anchor 30. The suture 32 is then tensioned to hold the anchor 30 in place.

The point 76 on the inner member 92 is then moved into engagement with an imperforate outer surface 130 (FIG. 1) on a human patient's skin 132. Manual force is applied to the handle 22 to cause the point 76 on the inner member 92 to pierce the surface 130. As this occurs, a circular opening is formed in the skin 132 by the point 76 of the inner member 92. This opening is formed directly ahead of and in axial alignment with the anchor 30.

The manual application of downward (as viewed in FIG. 1) force against the handle 122 moves the point 76 of the inner member 92 through the skin 132 into flesh 134 disposed beneath the skin. As this occurs, the leading end portion 44 of the anchor 30 moves into the opening which was initially formed by the point 76 on the inner member 92. The annular pusher surface 98 on the outer member 94 presses against the annular trailing end surface 42 of the anchor 30 to push the anchor into the body tissue.

Movement of the leading end portion 44 of the anchor 30 into the opening formed by the point 76 in the body tissue is facilitated by having at least a portion of the leading end surface 46 of the anchor 30 slope radially outward as a continuation of the surface 80 on the point 76. As the leading end 44 of the anchor 30 is pressed against the viscoelastic body tissue 88, the initial opening is elastically expanded and the anchor 30 moves into the flesh 134 disposed beneath the skin 132. The point 76 pierces the flesh 134 ahead of the anchor 30 to initiate the formation of an opening in the flesh for the anchor.

Continued application of force to the handle 22 results in the shaft 24 moving the anchor 30 to a desired depth in the body tissue 88. As this occurs, the point 76 on the inner member 92 continues to penetrate or pierce the body tissue 88 ahead of the anchor 30. This facilitates movement of the shaft 24 and anchor 30 into the body tissue 88.

The anchor 30 is moved into the body tissue 88 under the influence of force transmitted from the pusher surface 98 on the outer member 94 to the trailing end surface 42 of the anchor. Thus, as the shaft 24 and anchor 30 move into the body tissue 88, the outer member 94 is stationary relative to the inner member 92. The pusher surface 98 on the outer member 94 presses against the trailing end portion 38 of the anchor 30 with a force sufficient to move the anchor into the body tissue 88.

Once the anchor 30 has been moved into the body tissue 88, the anchor and shaft 24 are separated. When this is to be done, any tension in the legs 62 and 64 of the suture is eliminated. The actuator knob 112 is then moved downward (as viewed in FIG. 1) along the slot 114. As this occurs, relative movement between the anchor 30 and the inner member 92 results in the point 76 (FIG. 2) on the inner member being circumscribed by the tubular side wall 36 of the anchor.

When the anchor 30 is being separated from the inserter 20, the anchor may be pushed off of the end of the inner member 92 by the outer member 94 while the inner member remains stationary relative to the body tissue. Alternatively, the handle 22 and inner member 92 may be moved upwardly and the anchor 30 and outer member 94 maintained stationary relative to the body tissue. It is contemplated that, in all probability, there will be a combined movement of the anchor 30 and outer member 94 axially along the inner member 92 and withdrawal of the inner member from the body tissue as the anchor is separated from the shaft 24.

Changing Anchor Orientation

As the anchor 30 is separated from the shaft 24, it may remain in the orientation shown in FIG. 1 relative to the body tissue 88 and the shaft. Alternatively, the anchor 30 may be moved through the orientation shown in FIG. 4 to the orientation shown in FIG. 5. At least a portion of this movement of the anchor 30 occurs while the leading end portion 26 of the inserter 20 is in the passage 28 in the anchor.

During movement of the anchor 30 to a desired depth in the body tissue 88 (FIG. 1), the outer side surface 120 on the inner member 92 positions the anchor in a coaxial relationship with the inner member 92 and retains the anchor against pivotal movement. When the anchor 30 has been moved to the desired depth in the body tissue 88, the actuator 110 is manually operated. This causes relative movement between the inner and outer members 92 and 94.

As relative movement occurs between the inner and outer members 92 and 94, the point 76 on the outer member and the pusher surface 98 on the inner member move toward each other (FIG. 4). As this occurs, the positioning surface 120 on the inner member 92 almost moves out of the passage 28 in the anchor 30 (FIG. 4). This releases the anchor 30 for pivotal movement relative to the shaft 24. Although a major portion of the positioning surface 120 has been withdrawn from the anchor passage 28, the point 76 on the inner member 92 and the outermost portion of the positioning surface 120 are disposed in the passage 28 in the anchor.

Pivotal movement of the anchor 30 is then initiated by tensioning the outer leg 62 of the suture 32, as indicated by the arrow 84 in FIG. 4. The tension force applied to the leading end portion 44 of the anchor 30 causes it to rotate in a clockwise direction toward the position shown in FIG. 4. As the anchor approaches the position shown in FIG. 4, the inner side surface 52 on the anchor 30 moves into engagement with the outer side surface 80 on the point 76. This results in the transmittal of force from the outer side surface 80 of the point 76 to the inner side surface 52 of the anchor 30 in a downward (as viewed in FIG. 4) direction to further promote pivotal movement of the anchor in a clockwise direction.

As the outer member 94 continues to push downward (as viewed in FIG. 4) against the trailing end surface 42 of the anchor 30, the anchor continues to pivot relative to the shaft 24. The anchor 30 pivots about a location where the trailing end surface 42 of the anchor engages the outer member 94. In addition, the anchor 30 pivots about a location where the point 76 engages the inner side surface 52 of the anchor. This combined pivotal movement is caused by the tension in the outer leg 62 of the suture 32.

As the pusher surface 98 approaches and then moves past the base of the point 76, the point moves out of the passage 28 through the anchor 30. The anchor 30 then continues to pivot in a clockwise direction under the influence of the force applied to the anchor by the tension in the outer leg 62 of the suture 32. This force causes the anchor to move to the position shown in FIG. 5, or at least to a position closely approximating the position shown in FIG. 5. Once the anchor 30 has moved to the position shown in FIG. 5 relative to the body tissue 88, the relatively large outer side surface 50 of the anchor resists pulling out of the anchor from the body tissue. Therefore, relatively large forces can be transmitted through the suture 32 to the anchor 30 without pulling the anchor out of the body tissue.

When the anchor 30 is to be inserted into bone with the inserter 20, an opening is drilled through the hard outer layer of the bone into the soft inner material of the bone. Once this has been done, the inserter 20 is used to position the anchor 30 in the spongy cancellous tissue within the bone. The orientation of the anchor 30 may be changed, relative to the bone, in the same manner as previously explained herein.

It should be understood that it is contemplated that the inserter 20 may be used to position an anchor 30 in either hard or soft tissue at many different locations in a patient's body. The pointed end 76 of the inserter 20 may be used to pierce body tissue at locations remote from the patient's skin 132 (FIG. 1). Thus, the inserter 20 may be used to position an anchor in an organ disposed within the patient's body.

When the inserter 20 is to be used to position the anchor 30 in a preformed opening in hard body tissue, such as the hard outer or cortical layer of bone, the inner member 92 may not extend past the leading end portion 44 of the anchor 30. When the inserter 20 is to be used to position the anchor 30 in soft body tissue, the formation of an opening in the body tissue for the anchor 30 may be accomplished without piercing the body tissue with the inner member 92 and the inner member may not extend past the anchor. However, it is believed that it may be preferred to have the point 76 extend ahead of the anchor 30 even when the point is not to be used to pierce body tissue.

Inserter—Second Embodiment

In the embodiment of the inserter illustrated in FIGS. 1–5, the shaft 24 is formed by two members, that is, the inner member 92 and the outer member 94. In the embodiment of the inserter illustrated in FIGS. 6–9, the shaft of the inserter is formed by a single member. Since the embodiment of the invention illustrated in FIGS. 6–9 is generally similar to the embodiment of the invention illustrated in FIGS. 1–5, similar numerals will be utilized to designate similar components, the suffix letter "a" being associated with the numerals of FIGS. 6–9 to avoid confusion.

A suture anchor inserter 20a (FIG. 6) includes a manually engageable handle 22a and a one piece shaft 24a which extends outward from the handle. A leading end portion 26a of the one piece shaft 24a extends through a passage 28a in the suture anchor 30a. A suture 32a extends through the passage 28a in the anchor 30a and along the shaft 24a. The suture 32a extends through a passage (not shown) in the handle 22a. The anchor 30a has the same construction as the anchor 30 in the embodiment of the invention illustrated in FIGS. 1–5.

In accordance with a feature of the embodiment of the invention illustrated in FIGS. 6–9, the shaft 24a of the inserter 20a is formed as one piece. Thus, the shaft 24a includes a main section 142 (FIGS. 6 and 7) and a leading end section 144 (FIG. 7). The leading end section 144 includes a cylindrical positioning portion 146 which is disposed in a coaxial relationship with the cylindrical main section 142. A generally conical point 76a is formed on the leading end section 144 and has a conical outer side surface 80a.

A pusher surface 98a forms a flat annular shoulder where the cylindrical main section 142 is connected with the leading end section 144 of the shaft 24a. Since the shaft 24a is formed from a single piece of material, that is, stainless steel, the pusher surface 98a does not move relative to the point 76a of the shaft 24a. Although it is preferred to form the shaft 24a from a single piece of metal, the shaft may be formed by a solid cylindrical inner member and a cylindrical tubular outer member which is fixedly connected to the inner member. When the shaft 24a is formed by two fixedly connected members, the members may be different materials.

Figure 8:
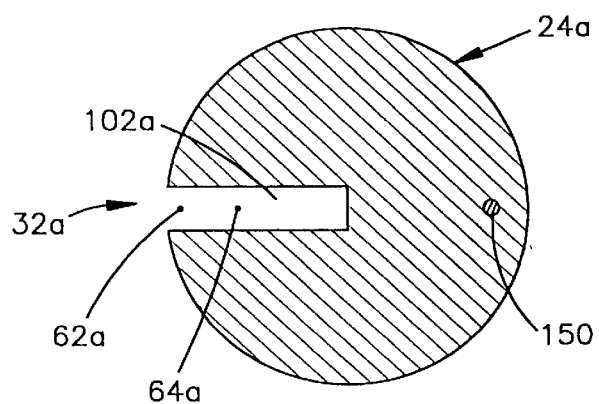
FIG. 8 is a sectional view, taken generally along the line 8—8 of FIG. 7, further illustrating the construction of the shaft of the inserter.

A slot 102a (FIGS. 7 and 8) extends from the base of the point 76a along the shaft 24a. The depth of the slot 102a is greater in the main section 142 (FIG. 7) of the one piece shaft 24a than in the leading end section 144 of the shaft. The inner and outer legs 62a and 64a of the suture 32a are received in the slot 102a (FIG. 8).

When the anchor 30a is to be inserted into human body tissue 88a (FIG. 6), the anchor is first positioned on the leading end section 144 of the shaft 24a with the suture 32a extending through the passage 28a in the anchor 30a. Thus, the anchor 30a is telescopically moved onto the positioning portion 146 of the leading end section 144 of the shaft 24a. As this occurs, a trailing end surface 42a on the anchor 30a is positioned in abutting engagement with the annular pusher surface 98a.

A cylindrical outer side surface 120a on the positioning portion 146 engages a cylindrical inner side surface 52a of the anchor 30a (FIG. 7). The positioning surface 120a on the leading end section 144 of the shaft 24a positions the anchor 30a in a coaxial relationship with the shaft 24a and the point 76a. The two legs 62a and 64a of the suture 32a are tensioned to hold the trailing end surface 42a of the anchor 30a in abutting engagement with the pusher surface 98a on the shaft 24a.

The point 76a on the leading end section 144 of the shaft 24a is then moved into engagement with an imperforate outer surface 130a (FIG. 6) of a human patient's skin 132a. A downward force is then manually applied to the handle 22a. This force causes the point 76a on the shaft 24a to pierce the outer side surface 130a of the skin 132a. The point 76a then moves into flesh 134a disposed beneath the skin. As this occurs, an opening is formed by the point 76a in the skin 132a.

The anchor 30a moves into the opening in the skin 132a. Force is applied against the trailing end surface 42a of the anchor 30a by the pusher surface 98a to push the anchor into the body tissue 88a. A leading end surface 46a on the anchor 30a is sloped so as to form a continuation of the outer side surface 80a of the point 76a. This results in a smooth enlargement or stretching of the circular opening which is initially formed in the skin 132a by the point 76a of the shaft 24a. As the shaft 24a and anchor 30a continue to move downward (as viewed in FIG. 6) into the flesh 134a beneath the skin 132a, the point 76a on the shaft 24a pierces the body tissue to facilitate movement of the anchor 30a into the body tissue.

Once the anchor 30a has been moved to the desired depth in the body tissue, the anchor is separated from the shaft 24a. This may be done by merely withdrawing the leading end section 144 of the shaft 24a from the anchor 30a while the anchor remains in the orientation shown in FIG. 6 in the body tissue 88a. It is contemplated that there will be relatively little friction between the outer side surface 120a on the positioning portion 146 of the shaft 24a and the inner side surface 52a. This enables the anchor to be held in position in the body tissue 88a by the resilient force applied against the anchor 30a by the body tissue as the inserter 20a is withdrawn from the anchor.

It is contemplated that it may be desired to apply force against the trailing end surface 42a of the anchor 30a to facilitate separation of the shaft 24a from the anchor 30a. If this is the case, a cylindrical pusher rod 150 (FIG. 7) may be provided in a suitable passage formed in the solid shaft 24a. An actuator 110a has a knob 112a which is connected with the pusher rod 150 and is movable along a slot 114a formed in the handle 22a.

When the shaft 24a is to be withdrawn from the anchor 30a, the actuator knob 112a is moved downward. This results in the pusher rod 150 moving downward (as viewed in FIG. 7) relative to the shaft 24a. A circular leading end surface on the pusher rod 150 applies force against the trailing end surface 42a of the anchor to facilitate separation of the shaft from the anchor. It should be understood that the pusher rod 150 is optional and may be omitted if desired.

It is believed that in certain situations at least, it will be desired to change the orientation of the anchor relative to the body tissue 88*a* and the shaft 24*a* as the shaft 24*a* and anchor 30*a* are separated. To accomplish this, the leg 62*a* of the suture 32*a* is tensioned, in the manner indicated by the arrow 84*a* in FIG. 9 as the shaft 24*a* is withdrawn from the anchor. This results in pivoting movement of the anchor relative to the shaft 24*a* in the same manner as previously explained in conjunction with the embodiment of the invention illustrated in FIGS. 1–5.

It is believed that the use of the pusher rod 150 to apply force against a side of the anchor 30*a* opposite from the suture 32*a* will promote pivoting movement of the anchor. In addition, pivoting movement of the anchor 30*a* is promoted by engagement of the outer side surface 80*a* on the point 76*a* of the shaft 24*a* with the inner side surface 52*a* of the anchor. It should be understood that the anchor 30*a* moves through the orientation shown in FIG. 9 to the orientation shown in FIG. 5 for the anchor 30.

It is contemplated that the point 76*a* may have a configuration which is different than the illustrated conical configuration. For example, the point 76*a* could be formed by a single flat side surface which is skewed relative to a central axis of the shaft 24 or by a plurality of skewed flat side surfaces which intersect at the central axis of the shaft. Alternatively, the end of the end section could have a blunt or flat configuration rather than the illustrated pointed configuration.

Third Embodiment of Inserter

In the embodiments of the inserter illustrated in FIGS. 1–9, the anchor is retained on the shaft of the inserter prior to insertion of the anchor into body tissue by tensioning the suture. In the embodiment of the invention illustrated in FIG. 10, the inserter includes a spring which is utilized to retain the anchor on the shaft of the inserter. Since the embodiment of the invention illustrated in FIG. 10 is generally similar to the embodiments of the invention illustrated in FIGS. 1–9, similar numerals will be utilized to designate similar components, the suffix letter "b" being associated with the numerals of FIG. 10 to avoid confusion.

An inserter 20*b* (FIG. 10) includes a handle (not shown) and a shaft 24*b* which extends outward from the handle. The shaft 24*b* is integrally formed from a single piece of metal, that is, stainless steel. The shaft 24*b* includes a relatively large diameter main section 142*b* and a relatively small diameter leading end section 144*b*. The leading end section 144*b* includes a positioning portion 146*b* on which a conical point 76*b* is disposed in a coaxial relationship with the main section 142*b* of the shaft 24*b*. An annular pusher surface 98*b* is formed at the junction between the main section 142*b* and positioning portion 146*b* of the shaft 24*b*.

A suture 32*b* has an outer leg 62*b* which extends along the outside of an anchor 30*b*. In addition, the suture 32*b* has an inner leg 64*b* which extends through a passage 28*b* in the anchor 30*b*. The leading end section 144*b* and the inner leg 62*b* of the suture 32*b* both extend through the passage 28*b* in the anchor 30*b*.

In accordance with a feature of this embodiment of the invention, a spring 160 extends through a passage in the shaft 24*b*. The illustrated spring 160 is formed of metal wire, However, the spring 160 could be a leaf spring formed of sheet metal if desired.

An upper end portion (not shown) of the wire spring 160 is connected with an actuator knob, corresponding to the actuator knobs 112 and 112*a* of the embodiments of the invention illustrated in FIGS. 1–9. The spring 160 has a bent portion 164 which engages an inner side surface 52*b* of the anchor 30*b*.

After the anchor 30*b* has been inserted into body tissue, in the manner described in conjunction with the embodiment of the invention illustrated in FIGS. 1–9, the spring 160 is axially tensioned. To axially tension the spring 160, the actuator knob is moved away from the leading end section 144*b* of the shaft 24*b*. The axial tension causes the bent portion 164 of the spring 160 to straighten and move out of engagement with the inner side surface 52*b* of the passage 28*b* in the anchor 30*b*. The shaft 24*b* can then be withdrawn from the anchor 30*b*.

It is preferred to move the bent portion 164 of the spring 160 out of engagement with the inner side surface 52*b* of the anchor 30*b* by resiliently flexing the spring. However, the tension force applied to the spring 160 may only effect a reduction in the force applied by the spring against the inner side surface 52*b* of the anchor 30*b*.

In the embodiment of the invention illustrated in FIG. 10, the anchor 30*b* and one-piece shaft 24*b* are separated by merely withdrawing the shaft from the anchor after it has been positioned in a desired location in body tissue. However, a pusher member, corresponding to the pusher rod 150 of the embodiment of the invention illustrated in FIGS. 6–9 could be utilized to promote separation of the anchor 30*b* from the shaft 24*b* if desired. Alternatively, the shaft 24*b* could be formed by two relatively movable members, corresponding to the inner and outer members 92 and 94 of the embodiment of the invention illustrated in FIGS. 1–5. Of course, the orientation of the anchor 30*b* can be changed relative to the shaft 24*b* by tensioning the leg 64*b* of the suture 32*b* as the point 76*b* of the shaft 24*b* moves to a location adjacent to the trailing end surface 42*b* of the anchor.

Conclusion

In view of the foregoing description, it is apparent that the present invention provides a new and improved suture anchor inserter 20 and method of using the suture anchor inserter. The suture anchor inserter 20 includes a handle 22 and a shaft 24 which extends outward from the handle. The shaft 24 has a leading end portion 72 which extends into an anchor 30. The leading end portion 72 of the shaft 24 may be pointed to facilitate piercing of body tissue 88 by the leading end portion of the shaft.

Once the anchor 30 has been inserted into the body tissue 88, it may be desired to change the orientation of the anchor relative to the body tissue. The orientation of the anchor 30 relative to the body tissue 88 may be changed by applying force against an inner side surface 52 of the anchor with the leading end portion 72 of the shaft 24. In one embodiment (FIGS. 1–5) of the inserter 20, a portion 94 of the shaft 24 is movable relative to another portion 92 of the shaft to facilitate separation of the anchor 30 and shaft. In the embodiment of the inserter illustrated in FIGS. 6–9, the shaft 24*a* is formed as one piece. A spring 160 (FIG. 10) may advantageously be utilized to hold the anchor 30 on the leading end portion of the shaft 24.

Having described the invention, the following is claimed:

1. A method of positioning a suture anchor in body tissue, said method comprising the steps of providing an anchor which has a passage which extends between first and second surface areas on the anchor, providing an inserter having an end portion and a pusher surface which is spaced from the end portion, and moving the anchor and inserter together into body tissue with the end portion of the inserter extending into the passage in the anchor and the pusher surface on the inserter engaging the second surface area on the anchor, said step of moving the anchor and inserter together into the body tissue includes transmitting force from the pusher surface on the inserter to the second surface area on the anchor.

2. A method as set forth in claim 1 further including the step of separating the inserter and the anchor after performing said step of moving the anchor and inserter together into body tissue, said step of separating the inserter and the anchor includes moving the end portion of the inserter out of the passage in the anchor.

3. A method as set forth in claim 2 wherein said step of separating the anchor and the inserter includes moving the pusher surface toward the end portion of the inserter.

4. A method as set forth in claim 2 wherein said step of separating the inserter and the anchor includes applying force against the second surface area on the anchor and moving the anchor relative to the end portion of the inserter under the influence of the force applied against the second surface area on the anchor.

5. A method as set forth in claim 1 wherein said step of moving the anchor and inserter together into body tissue includes initiating the formation of an opening in a surface area on the body tissue with the end portion of the inserter at a location ahead of the first surface area on the anchor.

6. A method as set forth in claim 1 wherein said step of moving the anchor and inserter together into body tissue includes penetrating the body tissue with the end portion of the inserter at a location ahead of the first surface area on the anchor.

7. A method as set forth in claim 1 further including the step of inserting a suture through an opening in the anchor, said step of moving the anchor and inserter together into body tissue is performed with the suture extending through the opening in the anchor.

8. An apparatus comprising an anchor having a passage which extends between first and second surface areas on the anchor, a suture disposed in engagement with said anchor, a manually engageable handle, and a shaft extending from said handle through the passage in said anchor, said shaft having a pointed end which extends away from the first surface area on said anchor in a direction away from said handle, said shaft having a pusher surface which is spaced from the pointed end of said shaft by a distance which is the same as a distance between the first and second surface areas on said anchor, said pointed end of said shaft being effective to penetrate body tissue in advance of said anchor and said pusher surface being effective to apply force against the second surface area on said anchor upon insertion of said anchor into body tissue.

9. An apparatus as set forth in claim 8 wherein said pusher surface is movable relative to said pointed end of said shaft to move said anchor relative to said pointed end of said shaft.

10. An apparatus for use in positioning a suture anchor relative to body tissue, said apparatus comprising a handle, an inner member having a first end portion fixedly connected with said handle and a second end portion which is spaced from said handle, said second end portion of said inner member being at least partially disposed in a passage in the anchor during insertion of the anchor into body tissue, and a tubular outer member at least partially enclosing said inner member, said outer member being slidable along said inner member between a retracted position in which an end surface on said outer member is spaced a first distance from said handle and an extended position in which the end surface on said outer member is spaced a second distance from said handle, said second distance being greater than said first distance, said end surface on said outer member being engageable with a first end portion of the anchor having a passage into which said inner member extends to block movement of the anchor along said inner member toward said handle during insertion of the anchor into body tissue with said outer member in the retracted position.

11. An apparatus as set forth in claim 10 wherein said second end portion of said inner member has surface means which extends outward from a second end portion of the anchor to penetrate body tissue ahead of the anchor during insertion of the anchor into body tissue with said outer member in the retracted position and said inner member partially disposed in the passage in the anchor.

12. An apparatus as set forth in claim 11 wherein said surface means on said second end portion of said inner member has a generally conical configuration and has a central axis which is coincident with a central axis of said inner member.

13. An apparatus as set forth in claim 10 wherein a first length of said inner member and a first length of said outer member are disposed in said handle in a telescopic relationship when said outer member is in the retracted position, a second length of said inner member and a second length of said outer member being disposed in said handle in a telescopic relationship when said outer member is in the extended position, said second length of said inner member and said second length of said outer member being shorter than said first length of said inner member and said first length of said outer member so that the extent of the telescopic relationship in said handle between said inner and outer members is greater when said outer member is in the retracted position than when said outer member is in the extended position.

14. A method of positioning a suture anchor in body tissue, said method comprising the steps of providing an inserter having a shaft with an end portion which extends into a passage in the anchor, moving the anchor into body tissue with the end portion of the shaft extending into the passage in the anchor and with a suture disposed in engagement with the anchor, and, thereafter, changing the orientation of the anchor relative to the body tissue and shaft while the end portion of the shaft is at least partially disposed in the passage in the anchor.

15. A method as set forth in claim 14 wherein said step of changing the orientation of the anchor relative to the body tissue and shaft includes tensioning the suture to apply force to the anchor and engaging an inner side surface of the passage in the anchor with the end portion of the shaft.

16. A method as set forth in claim 14 further including the step of reducing the extent to which the shaft extends into the passage in the anchor after moving the anchor into body tissue and prior to performance of said step of changing the orientation of the anchor relative to the body tissue and shaft.

17. A method as set forth in claim 14 wherein said step of moving the anchor into body tissue includes applying force against a trailing end surface of the anchor with a surface connected with the shaft of the inserter, said method further including the step of applying force against the trailing end surface of the anchor to move the anchor along the shaft of the inserter after moving the anchor into body tissue and prior to performance of said step of changing the orientation of the anchor relative to the body tissue and shaft.

18. A method as set forth in claim 14 wherein said step of moving the anchor into body tissue includes piercing an imperforate surface area on the body tissue with the end portion of the shaft while the end portion of the shaft extends into the passage in the anchor.

19. A method as set forth in claim 18 wherein said step of moving the anchor into body tissue further includes applying force against a trailing end surface of the anchor with the shaft to move a leading end surface of the anchor through an opening formed in the body tissue by piercing the body tissue with the end portion of the shaft.

20. A method as set forth in claim 14 wherein said step of changing the orientation of the anchor relative to the body tissue and shaft includes transmitting force through the suture to a first end portion of the anchor and applying force against an inner side surface of the passage in the anchor with the end portion of the shaft at a location adjacent to a second end portion of the anchor.

21. An apparatus for use in anchoring a suture in body tissue with an anchor having a passage which extends into the anchor, said apparatus comprising a handle, a shaft connected with said handle, said shaft extends outward from said handle and extends into the passage in the anchor during insertion of the anchor into body tissue, said shaft having a pusher surface which applies force against a trailing end portion of the anchor during insertion of the anchor into body tissue, and a pusher member which is movable relative to said shaft through an opening in said pusher surface to apply force against the trailing end portion of the anchor and effect relative movement between the anchor and said shaft with the anchor disposed in the body tissue to thereby facilitate separation of the anchor from said shaft.

22. An apparatus as set forth in claim 21 wherein said shaft is integrally formed as one piece, said pusher surface being disposed on said shaft in a fixed relationship with said shaft, said pusher member being movable relative to said shaft along a path which extends parallel to a longitudinal central axis of said shaft to apply force against the trailing end portion of the anchor.

23. An apparatus as set forth in claim 21 wherein said pusher member is at least partially disposed in a passage formed in said shaft.

24. An apparatus as set forth in claim 21 further including a spring which is connected with said shaft, said spring being movable relative to said shaft between a first position in which a portion of said spring engages an inner side surface of the passage in the anchor and a second position, said spring being effective to retain the anchor against movement relative to said shaft when said spring is in the first position, said spring being ineffective to retain the anchor against movement relative to said shaft when said spring is in the second position.

25. An apparatus as set forth in claim 21 wherein said shaft has a pointed end portion which extends ahead of a leading end portion of the anchor to pierce body tissue during inserting of the anchor into body tissue.

26. An apparatus for use in anchoring a suture in body tissue with an anchor having a passage which extends into the anchor, said apparatus comprising a handle, a shaft connected with said handle, said shaft extends outward from said handle into the passage in the anchor during insertion of the anchor into body tissue, and a spring which is connected with said shaft, said spring being movable relative to said shaft between a first position in which a portion of said spring engages an inner side surface of the passage in the anchor and a second position, said spring being effective to retain the anchor against movement relative to said shaft when said spring is in the first position, said spring being ineffective to retain the anchor against movement relative to said shaft when said spring is in the second position.

27. An apparatus as set forth in claim 26 wherein said shaft has a pusher surface which is fixedly connected with said handle and which applies force against a trailing end portion of the anchor during insertion of the anchor into body tissue, said apparatus further including a pusher member which is movable relative to said shaft through an opening in said pusher surface to apply force against the trailing end portion of the anchor and effect relative movement between the anchor and said shaft with the anchor disposed in the body tissue to thereby facilitate separation of the anchor from said shaft.

28. An apparatus as set forth in claim 26 wherein said shaft has a pointed end portion which extends ahead of a leading end portion of the anchor to pierce body tissue during insertion of the anchor into body tissue.

29. A method of positioning a suture anchor in body tissue, said method comprising the steps of engaging a surface area on body tissue with a leading end portion of a member which extends through an anchor engaged by a suture, piercing the surface area on the body tissue with the leading end portion of the member while the leading end portion of the member extends through the anchor, moving the leading end portion of the member and the anchor together into an opening formed in the body tissue during performance of said step of piercing the body tissue with the leading end portion of the member, withdrawing the leading end portion of the member from the anchor after moving the leading end portion of the member and the anchor together into the opening formed in the body tissue, and changing the orientation of the anchor relative to the leading end portion of the member as the leading end portion of the member is withdrawn from the anchor.

30. A method as set forth in claim 29 wherein said step of moving the leading end portion of the member and the anchor together into the opening formed in the body tissue includes transmitting force from the member to a trailing end of the anchor to move the anchor into the body tissue.

31. A method as set forth in claim 29 further including the steps of inserting a suture through a passage having openings in opposite ends of the anchor, and inserting the leading end portion of the member through the openings in the opposite ends of anchor with the suture in the openings in the opposite ends of anchor.

32. A method as set forth in claim 29 wherein said step of engaging the surface area on the body tissue with the leading end portion of the member includes engaging the surface area on body tissue with a pointed end of the member, said step of piercing the surface area on the body tissue includes initiating the formation of an opening in the surface area on the body tissue with the pointed end of the member.

33. A method as set forth in claim 29 wherein said step of moving the leading end portion of the member and the anchor together into an opening formed in the body tissue includes pressing a pusher surface against an end surface on the anchor and moving the anchor into the opening under the influence of force applied against the end surface on the anchor by the pusher surface while moving the leading end portion of the member relative to the body tissue.

34. A method as set forth in claim 29 wherein said step of withdrawing the leading end portion of the member from the anchor includes applying force against a trailing end portion of the anchor.

35. A method as set forth in claim 34 wherein said step of applying force against the end of the anchor includes moving a force transmitting surface relative to the member in a direction toward a leading end of the member.

36. A method as set forth in claim 29 wherein the leading end portion of the member includes a pointed end, said method further including the steps of moving the pointed end of the member through the anchor so that the pointed end of the member projects from a first side of the anchor, said step of piercing the surface area on the body tissue with the leading end portion of the member includes piercing the body tissue with the pointed end of the member, said step of changing the orientation of the anchor includes engaging an inner surface on the anchor with the pointed end of the member.

37. A method as set forth in claim 29 wherein said step of changing the orientation of the anchor relative to the leading end portion of the member includes tensioning the suture.

38. A method as set forth in claim 37 wherein said step of changing the orientation of the anchor includes applying force against a trailing end surface of the anchor.

39. A method of positioning a suture anchor in body tissue, said method comprising the steps of providing an anchor which engages a suture and has a passage which extends between first and second surface areas on the anchor, providing a member having an end portion which extends through the passage in the anchor to a position in which the end portion of the member extends a first distance from the first surface area on the anchor, moving the anchor into body tissue with the first surface area on the anchor leading, said step of moving the anchor into body tissue being performed with the end portion of the member extending the first distance ahead of the first surface area on the anchor and with the suture engaging the anchor, said step of moving the anchor into body tissue includes a applying force against an inner side surface of the passage in the anchor with a spring, and, thereafter, separating the member and the anchor while the anchor remains in the body tissue in engagement with the suture by moving the end portion of the member out of the passage in the anchor, said step of separating the member and the anchor includes flexing the spring to reduce force applied against the inner side surface of the passage in the anchor by the spring.

40. A method of positioning a suture anchor in body tissue, said method comprising the steps of providing an anchor which engages a suture and has a passage which extends between first and second surface areas on the anchor, providing a member having an end portion which extends through the passage in the anchor to a position in which the end portion of the member extends a first distance from the first surface area on the anchor, moving the anchor into body tissue with the first surface area on the anchor leading, said step of moving the anchor into body tissue being performed with the end portion of the member extending the first distance ahead of the first surface area on the anchor and with the suture engaging the anchor, and, thereafter, separating the member and the anchor while the anchor remains in the body tissue in engagement with the suture by moving the end portion of the member out of the passage in the anchor, said step of separating the member and the anchor includes transmitting force from a pusher surface to the second surface area on the anchor and moving the pusher surface relative to the member in a direction toward the end portion of the member, said step of moving the pusher surface relative to the member includes sliding a pusher element on which the pusher surface is disposed along the member in a direction toward the end portion of the member.

41. A method as set forth in claim 40 further including the steps of applying force against the second surface area on the anchor with the pusher surface during performance of said step of moving the anchor into body tissue.

42. A method as set forth in claim 40 wherein said step of moving the anchor into body tissue includes moving the pusher surface and the end portion of the member together relative to the body tissue, transmitting force from the pusher surface to the second surface area on the anchor, and pressing the first surface area on the anchor against the body tissue under the influence of force transmitted to the second surface area on the anchor from the pusher surface.

43. A method as set forth in claim 40 wherein said step of separating the member and the anchor includes moving the end portion of the member and the pusher surface together away from the anchor.

44. A method as set forth in claim 40 wherein said step of moving the anchor into body tissue includes a applying force against an inner side surface of the passage in the anchor with a spring, said step of separating the member and the anchor includes flexing the spring to reduce force applied against the inner side surface of the passage in the anchor by the spring.

45. A method as set forth in claim 40 wherein the suture extends through the passage in the anchor, said method further includes changing the orientation of the anchor relative to the member while the end portion of the member is disposed in the anchor.

46. A method of positioning a suture anchor in body tissue, said method comprising the steps of providing an anchor which engages a suture and has a passage which extends between first and second surface areas on the anchor, the suture extends through the passage in the anchor, providing a member having an end portion which extends through the passage in the anchor to a position in which the end portion of the member extends a first distance from the first surface area on the anchor, moving the anchor into body tissue with the first surface area on the anchor leading, said step of moving the anchor into body tissue being performed with the end portion of the member extending the first distance ahead of the first surface area on the anchor and with the suture engaging the anchor, thereafter, separating the member and the anchor while the anchor remains in the body tissue in engagement with the suture by moving the end portion of the member out of the passage in the anchor, and changing the orientation of the anchor relative to the member while the end portion of the member is disposed in the passage in the anchor along with the suture.

47. A method as set forth in claim 46 further including the steps of applying force against the second surface area on the anchor during performance of said step of moving the anchor into body tissue.

48. A method as set forth in claim 46 wherein said step of moving the anchor into body tissue includes moving a pusher surface and the end portion of the member together relative to the body tissue, transmitting force from the pusher surface to the second surface area on the anchor, and pressing the first surface area on the anchor against the body tissue under the influence of force transmitted to the second surface area on the anchor from the pusher surface.

49. A method as set forth in claim 48 wherein said step of separating the member and the anchor includes moving the pusher surface relative to the member in a direction toward the end portion of the member.

50. A method as set forth in claim 48 wherein said step of separating the member and the anchor includes moving the end portion of the member and the pusher surface together away from the anchor.

51. A method as set forth in claim 46 wherein said step of moving the anchor into body tissue includes a applying force against an inner side surface of the passage in the anchor with a spring, said step of separating the member and the anchor includes flexing the spring to reduce force applied against the inner side surface of the passage in the anchor by the spring.

52. A method as set forth in claim 46 wherein said step of separating the member and the anchor includes transmitting force from a pusher surface to the second surface area on the anchor and moving the pusher surface relative to the member in a direction toward the end portion of the member.

53. A method as set forth in claim 46 wherein said step of changing the orientation of the anchor relative to the member includes transmitting force from the suture to the anchor by tensioning the suture.

54. A method as set forth in claim 46 wherein said step of changing the orientation of the anchor relative to the member includes applying force against an inner side surface of the passage in the anchor with the member.

55. A method of positioning a suture anchor in body tissue, said method comprising the steps of providing an anchor which has a passage which extends between first and second surface areas on the anchor, providing an inserter having an end portion and a pusher surface which is spaced from the end portion, and moving the anchor and inserter together into body tissue with the end portion of the inserter extending into the passage in the anchor and the pusher surface on the inserter engaging the second surface area on the anchor, said step of moving the anchor and inserter together into the body tissue includes transmitting force from the pusher surface on the inserter to the second surface area on the anchor, said step of moving the anchor and inserter together into body tissue is performed with a suture extending through the passage in the anchor.

56. A method as set forth in claim 55 further including the step of separating the inserter and the anchor after performing said step of moving the anchor and inserter together into body tissue, said step of separating the inserter and the anchor includes moving the end portion of the inserter out of the passage in the anchor while the suture remains in the passage in the anchor.

57. A method as set forth in claim 56 wherein said step of separating the anchor and the inserter includes moving the pusher surface toward the end portion of the inserter.

58. A method as set forth in claim 56 wherein said step of separating the inserter and the anchor includes applying force against the second surface area on the anchor and moving the anchor relative to the end portion of the inserter under the influence of the force applied against the second surface area on the anchor.

59. A method as set forth in claim 55 wherein said step of moving the anchor and inserter together into body tissue includes initiating the formation of an opening in a surface area on the body tissue with the end portion of the inserter at a location ahead of the first surface area on the anchor.

60. A method as set forth in claim 55 wherein said step of moving the anchor and inserter together into body tissue includes penetrating the body tissue with the end portion of the inserter at a location ahead of the first surface area on the anchor.

61. A method as set forth in claim 55 further including the steps of separating the inserter and the anchor after having performed said step of moving the anchor and inserter together into body tissue, tensioning the suture, and changing the orientation of the anchor relative to the inserter while tensioning the inserter.

62. A method of positioning a suture anchor in body tissue, said method comprising the steps of providing an anchor which has a passage which extends between first and second surface areas on the anchor, providing an inserter having an end portion and a pusher surface which is spaced from the end portion, moving the anchor and inserter together into body tissue with the end portion of the inserter extending into the passage in the anchor and the pusher surface on the inserter engaging the second surface area on the anchor, said step of moving the anchor and inserter together into the body tissue includes transmitting force from the pusher surface on the inserter to the second surface area on the anchor, separating the inserter and the anchor after having performed said step of moving the anchor and inserter together into body tissue, and changing the orientation of the anchor relative to the inserter.

63. A method as set forth in claim 62 wherein said step of changing the orientation of the anchor relative to the inserter includes applying force against an inner side surface of the anchor with the end portion of the inserter.

64. A method as set forth in claim 62 wherein said step of changing the orientation of the anchor relative to the inserter includes tensioning the suture while engaging the second surface area on the anchor with the pusher surface.

65. A method as set forth in claim 62 wherein said step of changing the orientation of the anchor includes pivoting the anchor relative to the end portion of the inserter.

66. An apparatus comprising an anchor having a passage which extends between first and second surface areas on the anchor, a suture disposed in engagement with said anchor, a manually engageable handle, and a shaft extending from said handle through the passage in said anchor, said shaft having a pointed end which extends away from the first surface area on said anchor in a direction away from said handle, said shaft having a pusher surface which is spaced from the pointed end of said shaft by a distance which is the same as a distance between the first and second surface areas on said anchor, said pointed end of said shaft being effective to penetrate body tissue in advance of said anchor and said pusher surface being effective to apply force against the second surface area on said anchor upon insertion of said anchor into body tissue, said pusher surface being fixedly connected with said pointed end of said shaft.

67. An apparatus as set forth in claim 66 wherein said suture extends through at least a portion of the passage in said anchor.

68. An apparatus as set forth in claim 66 further including a spring which is connected with said shaft, said spring being movable relative to said shaft between a first position in which a portion of said spring engages an inner side surface of the passage in said anchor and a second position, said spring being effective to retain said anchor against movement relative to said shaft when said spring is in the first position, said spring being ineffective to retain said anchor against movement relative to said shaft when said spring is in the second position.

69. An apparatus as set forth in claim 66 further including a member which is movable relative to said shaft to move said anchor relative to said pointed end of said shaft.

70. An apparatus comprising an anchor having a passage which extends between first and second surface areas on the anchor, a suture disposed in engagement with said anchor and extending through at least a portion of the passage in said anchor, a manually engageable handle, and a shaft extending from said handle through the passage in said anchor, said shaft having a pointed end which extends away from the first surface area on said anchor in a direction away from said handle, said shaft having a pusher surface which is spaced from the pointed end of said shaft by a distance which is the same as a distance between the first and second surface areas on said anchor, said pointed end of said shaft being effective to penetrate body tissue in advance of said anchor and said pusher surface being effective to apply force against the second surface area on said anchor upon insertion of said anchor into body tissue.

71. An apparatus as set forth in claim 70 wherein said pusher surface is fixedly connected with said pointed end of said shaft.

72. An apparatus as set forth in claim 70 wherein said pusher surface is movable relative to said pointed end of said shaft to move said anchor relative to said pointed end of said shaft.

73. An apparatus as set forth in claim 70 further including a spring which is connected with said shaft, said spring being movable relative to said shaft between a first position in which a portion of said spring engages an inner side surface of the passage in said anchor and a second position, said spring being effective to retain said anchor against movement relative to said shaft when said spring is in the first position, said spring being ineffective to retain said anchor against movement relative to said shaft when said spring is in the second position.

74. An apparatus as set forth in claim 70 wherein said shaft includes a longitudinally extending inner section and an outer section which at least partially encloses and is movable along said inner section, said inner section having an end portion which is connected with said handle, said pointed end of said shaft being disposed on an end portion of said inner section which is opposite from the end portion of said inner section which is connected with said handle, said pusher surface being disposed on said outer section of said shaft.

75. An apparatus as set forth in claim 70 further including a member which is movable relative to said shaft to move said anchor relative to said pointed end of said shaft.

76. An apparatus comprising an anchor having a passage which extends between first and second surface areas on the anchor, a suture disposed in engagement with said anchor, a manually engageable handle, a shaft extending from said handle through the passage in said anchor, said shaft having a pointed end which extends away from the first surface area on said anchor in a direction away from said handle, said shaft having a pusher surface which is spaced from the pointed end of said shaft by a distance which is the same as a distance between the first and second surface areas on said anchor, said pointed end of said shaft being effective to penetrate body tissue in advance of said anchor and said pusher surface being effective to apply force against the second surface area on said anchor upon insertion of said anchor into body tissue, and a spring which is connected with said shaft, said spring being movable relative to said shaft between a first position in which a portion of said spring engages an inner side surface of the passage in said anchor and a second position, said spring being effective to retain said anchor against movement relative to said shaft when said spring is in the first position, said spring being ineffective to retain said anchor against movement relative to said shaft when said spring is in the second position.

77. An apparatus comprising an anchor having a passage which extends between first and second surface areas on the anchor, a suture disposed in engagement with said anchor, a manually engageable handle, and a shaft extending from said handle through the passage in said anchor, said shaft having a pointed end which extends away from the first surface area on said anchor in a direction away from said handle, said shaft having a pusher surface which is spaced from the pointed end of said shaft by a distance which is the same as a distance between the first and second surface areas on said anchor, said pointed end of said shaft being effective to penetrate body tissue in advance of said anchor and said pusher surface being effective to apply force against the second surface area on said anchor upon insertion of said anchor into body tissue, said shaft includes a longitudinally extending inner section and an outer section which at least partially encloses and is movable along said inner section, said inner section having an end portion which is connected with said handle, said pointed end of said shaft being disposed on an end portion of said inner section which is opposite from the end portion of said inner section which is connected with said handle, said pusher surface being disposed on said outer section of said shaft.

78. An apparatus for use in anchoring a suture in body tissue with an anchor having a passage which extends between first and second surface areas on the anchor, said apparatus comprising a handle, and a shaft connected with said handle, said shaft extends outward from said handle and extends through the passage in the anchor during insertion of the anchor into body tissue, said shaft having end surface means for piercing body tissue ahead of the first surface area on the anchor during insertion of the anchor into body tissue, said shaft having pusher surface means for transmitting force to the second surface area on the anchor to push the anchor during insertion of the anchor into body tissue, said shaft has positioning surface means for engaging an inner surface of the passage in the anchor to position the anchor relative to said pusher surface means and said end surface means, said positioning surface means extends through the passage in the anchor during insertion of the anchor into body tissue to position the anchor relative to said pusher surface means and said end surface means, said positioning surface means having an axial extent along a longitudinal central axis of said shaft equal to a distance between the first and second surface areas on the anchor.

79. An apparatus as set forth in claim 78 wherein said shaft is integrally formed as one piece, said pusher surface means being disposed on said shaft in a fixed relationship with said end surface means.

80. An apparatus as set forth in claim 78 further including a member which extends along and is movable relative to said shaft, said pusher surface means being disposed on said member which is movable along said shaft.

81. An apparatus as set forth in claim 78 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

82. An apparatus as set forth in claim 78 wherein said end surface means is pointed and has a generally conical configuration, and said pusher surface means has a generally annular configuration, said pointed end surface means and pusher surface means being disposed in a coaxial relationship.

83. An apparatus as set forth in claim 78 further including actuator means disposed adjacent to said handle and connected with said pusher surface means for moving said pusher surface means relative to said handle to move the anchor away from said handle and facilitate disengagement of the anchor from said shaft.

84. An apparatus as set forth in claim 78 wherein said pusher surface means is movable relative to said end surface means to move the anchor relative to said shaft to facilitate disengagement of the anchor from said shaft during insertion of the anchor into body tissue.

85. An apparatus as set forth in claim 84 further including actuator means disposed adjacent to said handle and connected with said pusher surface means, said actuator means being movable relative to said handle to move said pusher surface means relative to said end surface means.

86. An apparatus as set forth in claim 78 wherein said shaft includes an inner member which is connected with said handle and an outer member which at least partially encloses said inner member and is movable relative to said inner member, said pusher surface means being disposed on said outer member and being movable with said outer member relative to said inner member, said end surface means being disposed on said inner member, said positioning surface means being disposed on said inner member, said pusher surface means being movable along said positioning surface means upon relative movement between said inner and outer members.

87. An apparatus for use in anchoring a suture in body tissue with an anchor having a passage which extends between first and second surface areas on the anchor, said apparatus comprising a handle, and a shaft connected with said handle, said shaft extends outward from said handle and extends through the passage in the anchor during insertion of the anchor into body tissue, said shaft having end surface means for piercing body tissue ahead of the first surface area on the anchor during insertion of the anchor into body tissue, said shaft having pusher surface means for transmitting force to the second surface area on the anchor to push the anchor during insertion of the anchor into body tissue, said shaft being integrally formed as one piece, said pusher surface means being disposed on said shaft in a fixed relationship with said end surface means.

88. An apparatus for use in anchoring a suture in body tissue with an anchor having a passage which extends between first and second surface areas on the anchor, said apparatus comprising a handle, a shaft connected with said handle, said shaft extends outward from said handle and extends through the passage in the anchor during insertion of the anchor into body tissue, said shaft having end surface means for piercing body tissue ahead of the first surface area on the anchor during insertion of the anchor into body tissue, said shaft having pusher surface means for transmitting force to the second surface area on the anchor to push the anchor during insertion of the anchor into body tissue, and a member which extends along and is movable relative to said shaft, said pusher surface means being disposed on said member which is movable along said shaft.

89. An apparatus for use in anchoring a suture in body tissue with an anchor having a passage which extends between first and second surface areas on the anchor, said apparatus comprising a handle, a shaft connected with said handle, said shaft extends outward from said handle and extends through the passage in the anchor during insertion of the anchor into body tissue, said shaft having end surface means for piercing body tissue ahead of the first surface area on the anchor during insertion of the anchor into body tissue, said shaft having pusher surface means for transmitting force to the second surface area on the anchor to push the anchor during insertion of the anchor into body tissue, and a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

90. An apparatus for use in anchoring a suture in body tissue with an anchor having a passage which extends between first and second surface areas on the anchor, said apparatus comprising a handle, and a shaft connected with said handle, said shaft extends outward from said handle and extends through the passage in the anchor during insertion of the anchor into body tissue, said shaft having end surface means for piercing body tissue ahead of the first surface area on the anchor during insertion of the anchor into body tissue, said end surface means being pointed and having a generally conical configuration, said shaft having pusher surface means for transmitting force to the second surface area on the anchor to push the anchor during insertion of the anchor into body tissue, said pusher surface means has a generally annular configuration, said pointed end surface means and pusher surface means being disposed in a coaxial relationship.

91. An apparatus as set forth in claim 90 wherein said shaft has positioning surface means for engaging an inner surface of the passage in the anchor to position the anchor relative to said pusher surface means and said end surface means, said positioning surface means extends at least part way through the passage in the anchor during insertion of the anchor into body tissue to position the anchor relative to said pusher surface means and said end surface means.

92. An apparatus as set forth in claim 91 wherein said shaft includes an inner member which is connected with said handle and an outer member which at least partially encloses said inner member and is movable relative to said inner member, said pusher surface means being disposed on said outer member and being movable with said outer member relative to said inner member, said end surface means being disposed on said inner member, said positioning surface means being disposed on said inner member, said pusher surface means being movable along said positioning surface means upon relative movement between said inner and outer members.

93. An apparatus as set forth in claim 90 wherein said shaft is integrally formed as one piece, said pusher surface means being disposed on said shaft in a fixed relationship with said end surface means.

94. An apparatus as set forth in claim 90 further including a member which extends along and is movable relative to said shaft, said pusher surface means being disposed on said member which is movable along said shaft.

95. An apparatus as set forth in claim 90 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

96. An apparatus as set forth in claim 90 further including actuator means disposed adjacent to said handle and connected with said pusher surface means for moving said pusher surface means relative to said handle to move the anchor away from said handle and facilitate disengagement of the anchor from said shaft.

97. An apparatus as set forth in claim 90 wherein said pusher surface means is movable relative to said end surface means to move the anchor relative to said shaft to facilitate disengagement of the anchor from said shaft during insertion of the anchor into body tissue.

98. An apparatus as set forth in claim 89 further including actuator means disposed adjacent to said handle and connected with said pusher surface means, said actuator means being movable relative to said handle to move said pusher surface means relative to said end surface means.

99. An apparatus for use in anchoring a suture in body tissue with an anchor having a passage which extends between first and second surface areas on the anchor, said apparatus comprising a handle, a shaft connected with said handle, said shaft extends outward from said handle and extends through the passage in the anchor during insertion of the anchor into body tissue, said shaft having end surface means for piercing body tissue ahead of the first surface area on the anchor during insertion of the anchor into body tissue, said shaft having pusher surface means for transmitting force to the second surface area on the anchor to push the anchor during insertion of the anchor into body tissue, and actuator means disposed adjacent to said handle and connected with said pusher surface means for moving said pusher surface means relative to said handle to move the anchor away from said handle and facilitate disengagement of the anchor from said shaft.

100. An apparatus as set forth in claim 99 wherein said shaft has positioning surface means for engaging an inner surface of the passage in the anchor to position the anchor relative to said pusher surface means and said end surface means, said positioning surface means extends through the passage in the anchor during insertion of the anchor into body tissue to position the anchor relative to said pusher surface means and said end surface means, said positioning surface means having an axial extent along a longitudinal central axis of said shaft equal to a distance between the first and second surface areas on the anchor.

101. An apparatus as set forth in claim 100 wherein said shaft includes an inner member which is connected with said handle and an outer member which at least partially encloses said inner member and is movable relative to said inner member, said pusher surface means being disposed on said outer member and being movable with said outer member relative to said inner member, said end surface means being disposed on said inner member, said positioning surface means being disposed on said inner member, said pusher surface means being movable along said positioning surface means upon relative movement between said inner and outer members.

102. An apparatus as set forth in claim 99 further including a member which extends along and is movable relative to said shaft, said pusher surface means being disposed on said member which is movable along said shaft.

103. An apparatus as set forth in claim 99 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

104. An apparatus for use in anchoring a suture in body tissue with an anchor having a passage which extends between first and second surface areas on the anchor, said apparatus comprising a handle, and a shaft connected with said handle, said shaft extends outward from said handle and extends through the passage in the anchor during insertion of the anchor into body tissue, said shaft having end surface means for piercing body tissue ahead of the first surface area on the anchor during insertion of the anchor into body tissue, said shaft having pusher surface means for transmitting force to the second surface area on the anchor to push the anchor during insertion of the anchor into body tissue, said pusher surface means being movable relative to said end surface means to move the anchor relative to said shaft to facilitate disengagement of the anchor from said shaft during insertion of the anchor into body tissue.

105. An apparatus as set forth in claim 104 wherein said shaft has positioning surface means for engaging an inner surface of the passage in the anchor to position the anchor relative to said pusher surface means and said end surface means, said positioning surface means extends at least part way through the passage in the anchor during insertion of the anchor into body tissue to position the anchor relative to said pusher surface means and said end surface means.

106. An apparatus as set forth in claim 104 wherein said shaft includes an inner member which is connected with said handle and an outer member which at least partially encloses said inner member and is movable relative to said inner member, said pusher surface means being disposed on said outer member and being movable with said outer member relative to said inner member.

107. An apparatus as set forth in claim 104 further including a member which extends along and is movable relative to said shaft, said pusher surface means being disposed on said member which is movable along said shaft.

108. An apparatus as set forth in claim 104 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

109. An apparatus as set forth in claim 104 further including actuator means disposed adjacent to said handle and connected with said pusher surface means, said actuator means being movable relative to said handle to move said pusher surface means relative to said end surface means.

110. A method of positioning a suture anchor in body tissue, said method comprising the steps of providing an inserter having a shaft with an inner member and an outer member which partially encloses and which is movable relative to the inner member, said inner member having an end portion which extends outward from an end surface on the outer member and extends into the anchor, moving the anchor into body tissue with the inner member extending into the anchor and with the suture disposed in engagement with the anchor, said step of moving the anchor into body tissue includes transmitting force from the end surface on the outer member to a trailing end portion of the anchor, thereafter, separating the anchor and the outer member while the anchor remains in the body tissue, said step of separating the anchor from the outer member includes effecting relative movement between the inner and outer members while transmitting force between the trailing end portion of the anchor and the end surface on the outer member to decrease the extent to which the end portion of the inner member extends outward from the end surface on the outer member, and changing the orientation of the anchor relative to the body tissue and shaft of the inserter while performing said step of separating the anchor from the outer member, said step of changing the orientation of the anchor relative to the body tissue includes transmitting force between the end portion of the inner member and an inner surface of the anchor while transmitting force through the suture to the anchor.

111. A method as set forth in claim 110 wherein said step of moving the anchor into body tissue includes piercing the body tissue with the end portion of the inner member at a location ahead of the anchor.

112. A method as set forth in claim 110 wherein said step of moving the anchor into body tissue includes moving the anchor and the inner and outer members of the inserter into body tissue with the end portion of the inner member leading the anchor.

113. A method of positioning a suture anchor in body tissue, said method comprising the steps of engaging a surface area on the body tissue with a leading end portion of a suture anchor inserter which extends through a suture anchor engaged by a suture, piercing the surface area on the body tissue with the leading end portion of the suture anchor inserter while the suture anchor inserter extends through the suture anchor, and moving the leading end portion of the suture anchor inserter and the suture anchor together into an opening formed in the body tissue during performance of said step of piercing the body tissue with the leading end portion of the suture anchor inserter, said step of moving the leading end portion of the suture anchor inserter and suture anchor together into an opening formed in body tissue includes applying force against a trailing end portion of the suture anchor with the suture anchor inserter to prevent relative movement between the suture anchor inserter and the suture anchor.

114. A method as set forth in claim 113 further including the steps of inserting a suture through an opening in the anchor, and inserting the leading end portion of the suture anchor inserter into the opening in the suture anchor with the suture in the opening in the suture anchor, said step of inserting the leading end portion of the suture anchor inserter into the opening in the suture anchor includes sliding the leading end portion of the suture anchor inserter along a portion of the suture which extends generally parallel to a direction in which the leading end portion of the suture anchor inserter is moved into the suture anchor.

115. A method as set forth in claim 113 wherein said step of engaging the surface area on the body tissue with the leading end portion of the suture anchor inserter includes engaging the surface area on body tissue with a pointed end of the suture anchor inserter, said step of piercing the surface area on the body tissue includes initiating the formation of an opening in the surface area on the body tissue with the pointed end of the suture anchor inserter.

116. A method as set forth in claim 113 further including the step of withdrawing the leading end portion of the suture anchor inserter from the suture anchor after moving the leading end portion of the suture anchor inserter and the suture anchor together into the opening formed in the body tissue, said step of withdrawing the leading end portion of the suture anchor inserter from the suture anchor includes applying force against the trailing end portion of the suture anchor to push the suture anchor toward the leading end of the suture anchor inserter.

117. A method as set forth in claim 113 further including step of changing the orientation of the suture anchor relative to the leading end portion of the suture anchor inserter after moving the suture anchor into the body tissue.

118. A method as set forth in claim 117 wherein said step of changing the orientation of the suture anchor relative to the leading end portion of the suture anchor inserter includes tensioning the suture.

119. A method as set forth in claim 118 wherein said step of changing the orientation of the suture anchor includes applying force against a trailing end surface of the suture anchor.

120. A method as set forth in claim 113 further including step of disengaging the suture anchor from the leading end portion of the suture anchor inserter with the suture anchor in the body tissue, said step of disengaging the suture anchor from the leading end portion of the suture anchor inserter includes applying force against the trailing end portion of the suture anchor with the suture anchor inserter.

121. A method as set forth in claim 120 wherein said step of applying force against the trailing end of the suture anchor includes moving a force transmitting surface disposed on the suture anchor inserter in a direction toward a leading end of the suture anchor inserter.

122. An apparatus for use in anchoring a suture in body tissue with an anchor having a passage which extends between first and second surface areas on the anchor, said apparatus comprising a handle, and a shaft connected with said handle, said shaft extends outward from said handle and extends through the passage in the anchor during insertion of the anchor into body tissue, said shaft having end surface means for piercing body tissue ahead of the first surface area on the anchor during insertion of the anchor into body tissue, said shaft having positioning surface means for engaging an inner surface of the passage in the anchor to position the anchor relative to said shaft and said end surface means, said positioning surface means extends through the passage in the anchor during insertion of the anchor into body tissue to position the anchor relative to said shaft and said end surface means, said shaft having pusher surface means for transmitting force to the second surface area on the anchor to push the anchor during insertion of the anchor into body tissue, said pusher surface means projects outward of said positioning surface means to enable said pusher surface means to engage the second surface area on the anchor during insertion of the anchor into body tissue.

123. An apparatus as set forth in claim 122 wherein said shaft includes an inner member which is connected with said handle and an outer member which at least partially encloses said inner member and is movable relative to said inner member, said pusher surface means being disposed on said outer member and being movable with said outer member relative to said inner member, said end surface means being disposed on said inner member, said positioning surface means being disposed on said inner member, said pusher surface means being movable along said positioning surface means upon relative movement between said inner and outer members.

124. An apparatus as set forth in claim 122 wherein said shaft is integrally formed as one piece, said pusher surface means being disposed on said shaft in a fixed relationship with said positioning surface means and said end surface means.

125. An apparatus as set forth in claim 122 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

126. An apparatus as set forth in claim 122 wherein said end surface means is pointed and has a generally conical configuration, said positioning surface means has a generally cylindrical configuration, and said pusher surface means has a generally annular configuration, said end surface means, positioning surface means and pusher surface means being disposed in a coaxial relationship with said pusher surface means extending radially outward of said end surface means and positioning surface means.

127. An apparatus as set forth in claim 122 further including actuator means disposed adjacent to said handle and connected with said pusher surface means for moving said pusher surface means relative to said positioning surface means to move the anchor along said positioning surface means in a direction away from said handle.

128. An apparatus as set forth in claim 122 wherein said pusher surface means is movable relative to said positioning surface means and end surface means to move the anchor relative to said shaft to facilitate disengagement of the anchor from said shaft during insertion of the anchor into body tissue.

129. An apparatus as set forth in claim 128 further including actuator means disposed adjacent to said handle and connected with said pusher surface means, said actuator means being movable relative to said handle to move said pusher surface means relative to said positioning surface means.

* * * * *

(12) EX PARTE REEXAMINATION CERTIFICATE (5090th)
United States Patent
Bonutti

(10) Number: US 5,814,072 C1
(45) Certificate Issued: Mar. 29, 2005

(54) METHOD AND APPARATUS FOR USE IN ANCHORING A SUTURE

(75) Inventor: Peter M. Bonutti, Effingham, IL (US)

(73) Assignee: The Bonutti 2003 Trust-A, Effingham, IL (US)

Reexamination Request:
 No. 90/005,433, Aug. 9, 1999

Reexamination Certificate for:
| Patent No.: | 5,814,072 |
| --- | --- |
| Issued: | Sep. 29, 1998 |
| Appl. No.: | 08/752,005 |
| Filed: | Nov. 15, 1996 |

(51) Int. Cl.[7] .................................................. A61B 17/04
(52) U.S. Cl. ........................................ 606/232; 606/104
(58) Field of Search .......................................... 606/232

(56) References Cited

U.S. PATENT DOCUMENTS

| 4,235,238 A | * | 11/1980 | Ogiu et al. ................. 606/145 |
| --- | --- | --- | --- |
| 4,448,194 A | * | 5/1984 | DiGiovanni et al. ........ 606/145 |
| 4,741,330 A | * | 5/1988 | Hayhurst ..................... 606/144 |
| 5,002,550 A | * | 3/1991 | Li ............................... 606/139 |
| 5,041,129 A | * | 8/1991 | Hayhurst et al. ........... 606/232 |
| 5,059,206 A | * | 10/1991 | Winters ....................... 606/213 |
| 5,100,417 A | * | 3/1992 | Cerier et al. ................ 606/139 |
| 5,354,298 A | * | 10/1994 | Lee et al. .................... 606/72 |
| 5,403,348 A | * | 4/1995 | Bonutti ....................... 606/232 |
| 5,464,426 A | * | 11/1995 | Bonutti ....................... 606/232 |
| 5,549,630 A | * | 8/1996 | Bonutti ....................... 606/232 |
| 5,626,614 A | | 5/1997 | Hart ............................ 606/232 |

* cited by examiner

*Primary Examiner*—Gary Jackson

(57) ABSTRACT

A suture anchor inserter includes a manually engageable handle and a shaft which extends from the handle through a passage in the anchor. During insertion of the anchor into body tissue, an end portion of the shaft pierces the body tissue in advance of the anchor. At the same time, a pusher surface on the shaft applies force against a trailing end portion of the anchor to push the anchor into the body tissue. The shaft may be formed as one piece or may include an inner member which is enclosed by an outer member which is movable relative to the inner member. During insertion of the anchor into body tissue, it may be desired to change the orientation of the anchor relative to the body tissue and the shaft of the inserter. When the orientation of the anchor is to be changed, rotational force is applied to the anchor by tensioning the suture and pressing the end portion of the shaft against an inner surface of the passage in the anchor.

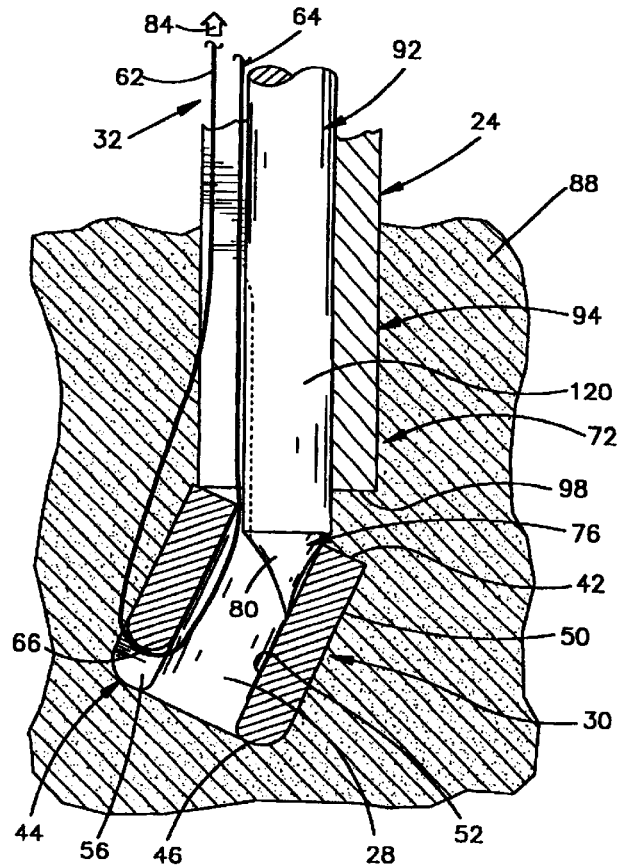

US 5,814,072 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13, 15, 16, 21–28, 31, 36, 38–54, 57, 61, 63, 68, 71, 73, 74, 76–86, 88, 89, 91, 94–96, 98–103, 105–112, 116 and 122–129 is confirmed.

Claims 1–12, 14, 17–20, 29, 30, 32–35, 37, 55, 56, 58–60, 62, 64–67, 69, 70, 72, 75, 87, 90, 92, 93, 97, 104, 113–115 and 117–121 are cancelled.

New claims 130–237 are added and determined to be patentable.

130. An apparatus as set forth in claim 13 wherein said second end portion of said inner member has surface means which extends outward from a second end portion of the anchor to penetrate body tissue ahead of the anchor during insertion of the anchor into body tissue with said outer member in the retracted position and said inner member partially disposed in the passage in the anchor.

131. An apparatus as set forth in claim 130 wherein said surface means on said second end portion of said inner member has a generally conical configuration and has a central axis which is coincident with a central axis of said inner member.

132. A method as set forth in claim 15 further including the step of reducing the extent to which the shaft extends into the passage in the anchor after moving the anchor into body tissue and prior to performance of said step of changing the orientation of the anchor relative to the body tissue and shaft.

133. A method as set forth in claim 15 wherein said step of moving the anchor into body tissue includes applying force against a trailing end surface of the anchor with a surface connected with the shaft of the inserter, said method further including the step of applying force against the trailing end surface of the anchor to move the anchor along the shaft of the inserter after moving the anchor into body tissue and prior to performance of said step of changing the orientation of the anchor relative to the body tissue and shaft.

134. A method as set forth in claim 15 wherein said step of moving the anchor into body tissue includes piercing an imperforate surface area on the body tissue with the end portion of the shaft while the end portion of the shaft extends into the passage in the anchor.

135. A method as set forth in claim 15 wherein said step of moving the anchor into body tissue further includes applying force against a trailing end surface of the anchor with the shaft to move a leading end surface of the anchor through an opening formed in the body tissue by piercing the body tissue with the end portion of the shaft.

136. A method as set forth in claim 16 wherein said step of moving the anchor into body tissue includes applying force against a trailing end surface of the anchor with a surface connected with the shaft of the inserter, said method further including the step of applying force against the trailing end surface of the anchor to move the anchor along the shaft of the inserter after moving the anchor into body tissue and prior to performance of said step of changing the orientation of the anchor relative to the body tissue and shaft.

137. A method as set forth in claim 16 wherein said step of moving the anchor into body tissue includes piercing an imperforate surface area on the body tissue with the end portion of the shaft while the end portion of the shaft extends into the passage in the anchor.

138. A method as set forth in claim 16 wherein said step of moving the anchor into body tissue further includes applying force against a trailing end surface of the anchor with the shaft to move a leading end surface of the anchor through an opening formed in the body tissue by piercing the body tissue with the end portion of the shaft.

139. A method as set forth in claim 16 wherein said step of changing the orientation of the anchor relative to the body tissue and shaft includes transmitting force through the suture to a first end portion of the anchor and applying force against an inner side surface of the passage in the anchor with the end portion of the shaft at a location adjacent to a second end portion of the anchor.

140. A method as set forth in claim 16 wherein said step of changing orientation of the anchor relative to the body tissue and shaft includes initiating the change in orientation of the anchor with the end portion of the shaft at least partially disposed in the passage in the anchor and continuing the change in the orientation of the anchor with the end portion of the shaft separate from the anchor.

141. A method as set forth in claim 16 wherein said step of changing the orientation of the anchor is performed with an outer side surface of the anchor in engagement with body tissue throughout the change in the orientation of the anchor.

142. A method as set forth in claim 16 wherein said step of moving the anchor into body tissue includes applying force against a trailing end portion of the anchor with a pusher surface, said step of reducing the extent which the shaft extends into the passage in the anchor includes moving the pusher surface relative to the shaft, said step of changing orientation of the anchor relative to the body tissue and the shaft includes pivoting the anchor about a location where the anchor engages the pusher surface.

143. A method as set forth in claim 31 wherein said step of moving the leading end portion of the member and the anchor together into the opening formed in the body tissue includes transmitting force from the member to a trailing end of the anchor to move the anchor into the body tissue.

144. A method as set forth in claim 31 wherein said step of engaging the surfarce area on the body tissue with the leading end portion of the member includes engaging the surface area on body tissue with a pointed end of the member, said step of piercing the surface area on the body tissue includes initiating the formation of an opening in the surface area on the body tissue with the pointed end of the member.

145. A method as set forth in claim 31 wherein said step of moving the leading end portion of the member and the anchor together into an opening formed in the body tissue includes pressing a pusher surface against an end surface on the anchor and moving the anchor into the opening under the influence of force applied against the end surface on the anchor by the pusher surface while moving the leading end portion of the member relative to the body tissue.

146. A method as set forth in claim 31 wherein said step of withdrawing the leading end portion of the member from the anchor includes applying force against a trailing end portion of the anchor.

147. A method as set forth in claim 146 wherein said step of applying force against the end of the anchor includes pressing a force transmitting member against a trailing end portion of the anchor with a central axis of the force transmitting member offset to one side of the central axis of the anchor.

148. A method as set forth in claim 31 wherein the leading end portion of the member includes a pointed end, said method further including the steps of moving the pointed end of the member through the anchor so that the pointed end of the member projects from a first side of the anchor, said step of piercing the surface area on the body tissue with the leading end portion of the member includes piercing the body tissue with the pointed end of the member, said step of changing the orientation of the anchor includes engaging an inner surface on the anchor with the pointed end of the member.

149. A method as set forth in claim 31 wherein said step of changing the orientation of the anchor relative to the leading end portion of the member includes tensioning the suture.

150. A method as set forth in claim 31 wherein said step of changing the orientation of the anchor includes applying force against a trailing end surface of the anchor with a member having a central axis which is offset to one side of a central axis of the anchor.

151. A method as set forth in claim 31 wherein said step of changing the orientation of the anchor relative to the leading end portion of the member includes pressing an outer side surface of the anchor against body tissue throughout performance of said step of changing the orientation of the anchor.

152. A method as set forth in claim 36 wherein said step of changing the orientation of the anchor includes applying force to a trailing end of the anchor at a location which is offset to one side of the pointed leading portion of the member to apply a torque to the anchor tending to rotate the anchor relative to the pointed leading end portion of the member.

153. A method as set forth in claim 38 wherein said step of moving the leading end portion of the member and the anchor together into the opening formed in the body tissue includes transmitting force from the member to the trailing end surface of the anchor to move the anchor into the body tissue.

154. A method as set forth in claim 38 further including the steps of inserting the suture through a passage having openings in opposite ends of the anchor, and inserting the leading end portion of the member through the openings in the opposite ends of anchor with the suture in the openings in the opposite ends of anchor.

155. A method as set forth in claim 38 wherein said step of engaging the surface area on the body tissue with the leading end portion of the member includes engaging the surface area on body tissue with a pointed end of the member, said step of piercing the surface area on the body tissue includes initiating the formation of an opening in the surface area on the body tissue with the pointed end of the member.

156. A method as set forth in claim 38 wherein said step of moving the leading end portion of the member and the anchor together into an opening formed in the body tissue includes pressing a pusher surface against an end surface on the anchor and moving the anchor into the opening under the influence of force applied against the end surface on the anchor by the pusher surface while moving the leading end portion of the member relative to the body tissue.

157. A method as set forth in claim 38 wherein said step of withdrawing the leading end portion of the member from the anchor includes applying force against a trailing end portion of the anchor with a member having a central axis which is offset to one side of a central axis of the anchor.

158. A method as set forth in claim 157 wherein said step of applying force against the end of the anchor includes moving a force transmitting surface relative to the member in a direction toward a leading end of the member.

159. A method as set forth in claim 157 wherein the leading end portion of the member includes a pointed end, said method further including the steps of moving the pointed end of the member through the anchor so that the pointed end of the member projects from a first side of the anchor, said step of piercing the surface area on the body tissue with the leading end portion of the member includes piercing the body tissue with the pointed end of the member, said step of changing the orientation of the anchor includes engaging an inner surface on the anchor with the pointed end of the member.

160. A method as set forth in claim 38 wherein said step of changing the orientation of the anchor relative to the leading end portion of the member includes transmitting force from an outer side surface of the anchor to the body tissue to deform body tissue throughout performance of said step of changing the orientation of the anchor.

161. A method as set forth in claim 38 wherein said step of withdrawing the leading end portion of the member from the anchor includes applying force against a trailing end portion of the anchor with a pusher surface, said step of changing the orientation of the anchor relative to the leading end portion of the member includes pivoting the anchor about a location where the trailing end portion of the anchor engages the pusher surface under the influence of force transmitted to the anchor by tensioning the suture.

162. A method as set forth in claim 161 further including the step of pressing an outer side surface of the anchor against body tissue during pivotal movement of the anchor relative to the leading end portion of the member.

163. A method as set forth in claim 57 wherein said step of separating the inserter and the anchor includes applying force against the second surface area on the anchor with the pusher surface and moving the anchor relative to the end portion of the inserter under the influence of the force applied against the second surface area on the anchor by the pusher surface.

164. A method as set forth in claim 57 wherein said step of moving the anchor and inserter together into body tissue includes initiating the formation of an opening in a surface area on the body tissue with the end portion of the inserter at a location ahead of the first surface area on the anchor.

165. A method as set forth in claim 57 wherein said step of moving the anchor and inserter together into body tissue includes penetrating the body tissue with the end portion of the inserter at a location ahead of the first surface area on the anchor.

166. A method as set forth in claim 57 further including the steps of tensioning the suture, and changing the orientation of the anchor relative to the inserter while tensioning the inserter.

167. A method as set forth in claim 57 wherein said step of separating the anchor and the inserter includes pressing the pusher surface against only a location on the anchor offset to one side of the end portion of the inserter.

168. A method as set forth in claim 57 wherein said step of separating the anchor and the inserter includes pivoting the anchor about a location where the pusher surface engages the anchor as the pusher surface moves toward the end portion of the inserter.

169. A method as set forth in claim 57 further including the step of deforming body tissue under the influence of force transmitted from the anchor to the body tissue throughout performance of said step of moving the pusher surface toward the end portion of the inserter.

170. A method as set forth in claim 63 wherein said step of changing the orientation of the anchor relative to the inserter includes tensioning the suture while engaging the second surface area on the anchor with the pusher surface.

171. A method as set forth in claim 63 wherein said step of changing the orientation of the anchor includes pivoting the anchor relative to the end portion of the inserter.

172. A method as set forth in claim 63 wherein said step of changing the orientation of the anchor relative to the inserter includes applying a torque to the anchor to rotate the anchor relative to the end portion of the inserter by applying force to a trailing end of the anchor at a location which is offset to one side of the end portion of the inserter.

173. A method as set forth in claim 63 wherein said step of separating the inserter and the anchor includes moving the pusher surface relative to the end portion of the inserter to push the anchor off the end portion of the inserter and pushing body tissue aside with a leading end portion of the anchor as the anchor is pushed off the end portion of the inserter.

174. A method as set forth in claim 63 wherein said step of changing the orientation of the anchor relative to the inserter includes pivoting the anchor about a location where the anchor engages the pusher surface.

175. A method as set forth in claim 63 wherein said step of applying force against an inner side surface of the anchor is at least partially performed during pivotal movement of the anchor.

176. An apparatus as set forth in claim 68 further including a member which is movable relative to said shaft to move said anchor relative to said pointed end of said shaft.

177. An apparatus as set forth in claim 71 further including a member having a central axis which is offset to one side of a central axis of said shaft, said member being movable along the central axis of said member to apply force against said anchor to move said anchor relative to said shaft.

178. An apparatus as set forth in claim 71 further including a member which is extendable from said pusher surface toward said pointed end of said shaft to apply force against a trailing end of said anchor to move the trailing end of said anchor away from said pusher surface.

179. An apparatus as set forth in claim 73 further including a member which is movable relative to said shaft to move said anchor relative to said pointed end of said shaft.

180. An apparatus as set forth in claim 91 wherein said shaft includes an inner member which is connected with said handle and an outer member which at least partially encloses said inner member and is movable relative to said inner member, said pusher surface means being disposed on said outer member and being movable with said outer member relative to said inner member, said end surface means being disposed on said inner member, said positioning surface means being disposed on said inner member, said pusher surface means being movable along said positioning surface means upon relative movement between said inner and outer members.

181. An apparatus as set forth in claim 91 wherein said shaft is integrally formed as one piece, said pusher surface means being disposed on said shaft in a fixed relationship with said end surface means.

182. An apparatus as set forth in claim 91 further including a member which extends along and is movable relative to said shaft, said pusher surface means being disposed on said member which is movable along said shaft.

183. An apparatus as set forth in claim 91 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

184. An apparatus as set forth in claim 91 further including actuator means disposed adjacent to said handle and connected with said pusher surface means for moving said pusher surface means relative to said handle to move the anchor away from said handle and facilitate disengagement of the anchor from said shaft.

185. An apparatus as set forth in claim 91 wherein said pusher surface means is movable relative to said end surface means to move the anchor relative to said shaft to facilitate disengagement of the anchor from said shaft during insertion of the anchor into body tissue.

186. An apparatus as set forth in claim 91 further including actuator means disposed adjacent to said handle and connected with said pusher surface means, said actuator means being movable relative to said handle to move said pusher surface means relative to said end surface means.

187. An apparatus as set forth in claim 94 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

188. An apparatus as set forth in claim 94 further including actuator means disposed adjacent to said handle and connected with said member which is movable along said shaft to move said pusher surface means relative to said handle to move the anchor away from said handle and facilitate disengagement of the anchor from said shaft.

189. An apparatus as set forth in claim 95 further including actuator means disposed adjacent to said handle and connected with said pusher surface means for moving said pusher surface means relative to said handle to move the anchor away from said handle and facilitate disengagement of the anchor from said shaft.

190. An apparatus as set forth in claim 96 wherein said shaft includes an inner member which is connected with said handle and an outer member which at least partially encloses said inner member and is movable relative to said inner member, said actuator means being connected with said handle and said outer member, said pusher surface means being disposed on said outer member and being movable with said outer member relative to said inner member, said end surface means being disposed on said inner member.

191. An apparatus as set forth in claim 96 further including a member which extends along and is movable relative to said shaft, said pusher surface means being disposed on said member which is movable along said shaft, said actuator means being connected with said handle and with said member which is movable along said shaft.

192. An apparatus as set forth in claim 96 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

193. An apparatus as set forth in claim 105 wherein said shaft includes an inner member which is connected with said handle and an outer member which at least partially encloses said inner member and is movable relative to said inner member, said pusher surface means being disposed on said outer member and being movable with said outer member relative to said inner member.

194. An apparatus as set forth in claim 105 further including a member which extends along and is movable relative to said shaft, said pusher surface means being disposed on said member which is movable along said shaft.

195. An apparatus as set forth in claim 105 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

196. An apparatus as set forth in claim 105 further including actuator means connected with said handle and said pusher surface means, said actuator means being movable relative to said handle to move said pusher surface means relative to said end surface means.

197. An apparatus as set forth in claim 106 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

198. An apparatus as set forth in claim 109 wherein said shaft has a positioning surface which is engagable with an inner surface of the passage in the anchor to position the anchor relative to said pusher surface means and said end surface means, said positioning surface is disposed in the passage in the anchor during insertion of the anchor into body tissue and is effective to position the anchor relative to said pusher surface means and said end surface means.

199. An apparatus as set forth in claim 109 wherein said shaft includes an inner member which is connected with said handle and an outer member which at least partially encloses said inner member and is movable relative to said inner member, said pusher surface means being disposed on said outer member and being movable with said outer member relative to said inner member.

200. An apparatus as set forth in claim 109 further including a pusher member which extends along and is movable relative to said shaft, said pusher member having a longitudinal central axis which is offset to one side of a longitudinal central axis of said shaft, said pusher surface means being disposed on said pusher member.

201. An apparatus as set forth in claim 109 further including a spring which is resiliently deflectable to move relative to said shaft between an engaged position in which said spring engages the inner surface of the passage in the anchor to retain the anchor against movement relative to said shaft and a disengaged position in which said spring is ineffective to retain the anchor against movement relative to said shaft.

202. A method as set forth in claim 116 further including the steps of inserting a suture through an opening in the anchor, and inserting the leading end portion of the suture anchor inserter into the opening in the suture anchor with the suture in the opening in the suture anchor, said step of inserting the leading end portion of the suture anchor inserter into the opening in the suture anchor includes sliding the leading end portion of the suture anchor inserter along a portion of the suture which extends generally parallel to a direction in which the leading end portion of the suture anchor inserter is moved into the suture anchor.

203. A method as set forth in claim 116 wherein said step of engaging the surface area on the body tissue with the leading end portion of the suture anchor inserter includes engaging the surface area on body tissue with a pointed end of the suture anchor inserter, said step of piercing the surface area on the body tissue includes initiating the formation of an opening in the surface area on the body tissue with the pointed end of the suture anchor inserter.

204. A method as set forth in claim 116 further including the step of changing the orientation of the suture anchor relative to the leading end portion of the suture anchor inserter after moving the suture anchor into the body tissue.

205. A method as set forth in claim 204 wherein said step of changing the orientation of the suture anchor relative to the leading end portion of the suture anchor inserter includes tensioning the suture and pivoting the suture anchor about a location where the suture anchor engages the suture anchor inserter.

206. A method as set forth in claim 204 wherein said step of changing the orientation of the suture anchor include pressing the suture anchor against body tissue throughout performance of said step of changing the orientation of the suture anchor.

207. A method of positioning a suture anchor in body tissue, said method comprising the steps of providing an anchor which has a passage which extends between first and second surface areas on the anchor, providing an inserter having an end portion and a pusher surface which is spaced from the end portion, moving the anchor and inserter together into body tissue with the end portion of the inserter extending into the passage in the anchor and the pusher surface on the inserter engaging the second surface area on the anchor, said step of moving the anchor and inserter together into the body tissue is performed with the anchor in a first orientation relative to the inserter and includes transmitting force from the pusher surface on the inserter to the second surface area on the anchor, and changing the orientation of the anchor relative to the inserter from the first orientation to a second orientation with an outer side surface of the anchor disposed in engagement with the body tissue throughout performance of said step of changing the orientation of the anchor from the first orientation to the second orientation.

208. A method as set forth in claim 207 wherein said step of changing the orientation of the anchor relative to the inserter from the first orientation to the second orientation includes tensioning the suture to initiate movement of the anchor from the first orientation toward the second orientation.

209. A method as set forth in claim 207 wherein said step of changing the orientation of the anchor from the first orientation to the second orientation includes pivoting the anchor about a location where the anchor engages the pusher surface.

210. A method as set forth in claim 207 wherein said step of changing the orientation of the anchor from the first orientation to the second orientation includes pressing the outer side surface of the anchor against the body tissue and deforming the body tissue under the influence of force transmitted from the outer side surface of the anchor to the body tissue throughout movement of the anchor from the first orientation to the second orientation.

211. A method of positioning a suture anchor in body tissue, said method comprising the steps of providing an anchor which has a passage which extends between first and second surface areas on the anchor, providing an inserter having an end portion and a pusher surface which is spaced from the end portion, moving the anchor and inserter together into body tissue with the end portion of the inserter extending into the passage in the anchor and the pusher surface on the inserter engaging the second surface area on the anchor, said step of moving the anchor and inserter together into the body tissue is performed with the anchor in a first orientation relative to the inserter and includes transmitting force from the pusher surface on the inserter to the second surface area on the anchor, and changing the orientation of the anchor relative to the inserter from the first orientation to a second orientation, said step of changing the orientation of the anchor relative to the inserter includes pivoting the anchor about a location where the anchor engages the pusher surface.

212. A method as set forth in claim 211 wherein said step of pivoting the anchor about the location where the anchor engages the pusher surface includes transmitting force to the anchor through the suture.

213. A method as set forth in claim 211 further including the step of applying force against body tissue with the anchor as the anchor pivots about the location where the anchor engages the pusher surface.

214. A method as set forth in claim 211 further including the step of engaging an inner side surface of the anchor with the end portion of the inserter during pivotal movement of the anchor relative to the inserter.

215. A method of positioning a suture anchor in body tissue, said method comprising the steps of providing an inserter having a shaft with an end portion which extends into a passage in the anchor, moving the anchor into body tissue with the end portion of the shaft extending into the passage in the anchor and with a suture disposed in engagement with the anchor, said step of moving the anchor into body tissue includes applying force against a trailing end portion of the anchor with a pusher surface, and, thereafter, changing the orientation of the anchor relative to the body tissue and shaft while the end portion of the shaft is at least partially disposed in the passage in the anchor and the pusher surface is in engagement with the trailing end portion of the anchor.

216. A method as set forth in claim 215 wherein said step of changing the orientation of the anchor relative to the body tissue includes transmitting force from the anchor to the body tissue throughout performance of said step of changing the orientation of the anchor relative to the body tissue.

217. A method as set forth in claim 215 wherein said step of changing the orientation of the anchor relative to the body tissue includes pivoting the anchor about a location where the pusher surface engages the trailing end portion of the anchor.

218. A method of positioning a suture anchor in body tissue, said method comprising the steps of providing an anchor which has a passage which extends between first and second surface areas on the anchor, providing an inserter having an end portion and a pusher surface which is spaced from the end portion, moving the anchor and inserter together into body tissue with the end portion of the inserter extending into the passage in the anchor and the pusher surface on the inserter engaging the second surface area on the anchor, said step of moving the anchor and inserter together into the body tissue includes transmitting force from the pusher surface on the inserter to the second surface area on the anchor, separating the inserter and the anchor after having performed said step of moving the anchor and inserter together into body tissue, and changing the orientation of the anchor relative to the inserter, said step of changing the orientation of the anchor relative to the inserter includes transmitting force from the anchor to the body tissue through performance of said step of changing the orientation of the anchor relative to body tissue.

219. A method as set forth in claim 218 wherein said step of changing the orientation of the anchor relative to the inserter includes pivoting the anchor about a location where the anchor engages the pusher surface.

220. A method as set forth in claim 218 wherein said step of changing the orientation of the anchor relative to the body tissue includes transmitting force to the anchor through the suture to press the anchor against the body tissue and deform the body tissue throughout movement of the anchor relative to the body tissue.

221. A method of positioning a suture anchor in body tissue, said method comprising the steps of moving the suture anchor into body tissue with a pointed end portion of an inserter extending into an opening in the suture anchor and with a suture connected with the suture anchor, and changing the orientation of the suture anchor relative to the pointed end portion of the inserter, said step of changing the orientation of the suture anchor relative to the pointed end portion of the inserter is at least partially performed while tensioning the suture with an outer side surface of the suture anchor disposed in engagement with body tissue and with the pointed end portion of the inserter in engagement with a surface of the suture anchor which at least partially forms the opening in the suture anchor.

222. A method as set forth in claim 221 wherein said step of changing the orientation of the suture anchor relative to the pointed end portion of the inserter includes sliding a tapered tip of the pointed end portion of the inserter and the surface of the suture anchor which at least partially forms the opening in the suture anchor relative to each other.

223. A method as set forth in claim 221 wherein said step of moving the suture anchor into body tissue includes deflecting body tissue under the influence of force transmitted from the inserter through the suture anchor to the body tissue.

224. A method as set forth in claim 221 wherein said step of moving the suture anchor into body tissue includes piercing the body tissue with the pointed end portion of the inserter.

225. A method as set forth in claim 221 wherein said step of moving the suture anchor into body tissue is performed with first and second sections of the suture extending from the suture anchor to a location outside of the body tissue, said step of changing the orientation of the suture anchor relative to the pointed end portion of the inserter while tensioning the suture includes tensioning at least one of the first and second sections of the suture.

226. A method as set forth in claim 221 further including the step of withdrawing the pointed end portion of the inserter form the opening in the suture anchor after having at least partially performed said step of changing the orientation of the suture anchor relative to the pointed end portion of the inserter.

227. A method as set forth in claim 226 wherein said step of changing the orientation of the suture anchor relative to the pointed end portion of the suture is at least partially performed after withdrawing the pointed end portion of the inserter from the opening in the suture anchor and includes deflecting body tissue under the influence of force transmitted from the suture through the suture anchor to the body tissue.

228. A method as set forth in claim 221 wherein said step of changing the orientation of the suture anchor relative to the pointed end portion of the inserter includes pivoting the suture anchor about a location where the surface of the suture anchor which at least partially forms the opening in the suture anchor engages the pointed end portion of the inserter.

229. A method as set forth in claim 228 further including the step of deflecting body tissue under the influence of force transmitted from the suture anchor to the body tissue while pivoting the suture anchor about the location where the surface of the suture anchor which at least partially forms the opening in the suture anchor engages the pointed end portion of the inserter.

230. A method of positioning a suture anchor in body tissue, said method comprising the steps of moving the suture anchor into body tissue with a pointed end portion of an inserter extending into an opening in the suture anchor and with a suture connected with the suture anchor, and changing the orientation of the suture anchor relative to the pointed end portion of the inserter, said step of changing the orientation of the suture anchor relative to the pointed end portion of the inserter includes pivoting the suture anchor about a location where the surface of the suture anchor which at least partially forms the opening in the suture anchor engages the pointed end portion of the inserter.

231. A method as set forth in claim 230 further including the step of deflecting body tissue under the influence of force transmitted from the suture anchor to the body tissue while pivoting the suture anchor about the location where the surface of the suture anchor which at least partially forms the opening in the suture anchor engages the pointed end portion of the inserter.

232. A method as set forth in claim 230 wherein said step of pivoting the suture anchor relative to the pointed end portion of the inserter is at least partially performed under the influence of force transmitted from the suture to the suture anchor by tensioning the suture.

233. A method of positioning a suture anchor in body tissue, said method comprising the steps of moving the suture anchor into body tissue with a pointed end portion of an inserter extending into an opening in the suture anchor and with a suture connected with the suture anchor, said step of moving the suture anchor into body issue is performed with the suture anchor in a first orientation relative to the inerter, and changing the orientation of the suture anchor from the first orientation to a second orientation relative to the inserter, said step of changing the orientation of the suture anchor from the first orientation to a second orientation includes partially withdrawing the pointed end portion of the inserter from the opening in the suture anchor, pivoting the suture anchor while the pointed end portion of the inserter is only partially withdrawn from the opening in the suture anchor by tensioning the suture, completely withdrawing the pointed end portion of the inserter from the opening in the suture anchor, and, hereafter, pivoting the suture anchor under the influence of force transmitted from the suture to the suture anchor.

234. A method as set forth in claim 233 wherein said step of changing the orientation of the suture anchor from the first to the second orientation is performed with an outer side surface of the suture anchor in engagement with body issue.

235. A method as set forth in claim 233 wherein said step of pivoting the suture anchor while the pointed end portion of the inserter is only partially withdrawn from the opening in the suture anchor includes deflecting body tissue under the influence of force transmitted from an outer surface of the suture anchor to the body tissue.

236. A method of positioning a suture anchor in body tissue, said method comprising the steps of moving the suture anchor into body tissue with a pointed end portion of an inserter extending into an opening in the suture anchor and with a suture connected with the suture anchor, said step of moving the suture anchor into body tissue is performed with a first end portion of the suture anchor leading and a second end portion of the suture anchor trailing, at least partially withdrawing the pointed end portion of the inserter from the opening in the suture anchor, thereafter, tensioning the suture, pivoting the suture anchor about the trailing end portion of the suture anchor under the influence of force transmitted to the suture anchor through the suture while tensioning the suture with the pointed end portion of the inserter only partially withdrawn from the suture anchor, and deflecting body tissue under the influence of force applied against the body tissue by an outer side surface area of the suture anchor while pivoting the suture anchor about the trailing end portion of the suture anchor with the pointed end portion of the inserter only partially withdrawn from the suture anchor.

237. A method as set forth in claim 236 wherein an initial portion of said step of pivoting the suture anchor about the trailing end portion of the suture anchor is performed while a portion of the pointed end portion of the inserter is disposed in the opening in the suture anchor and a final portion of the step of pivoting the suture anchor about the trailing end portion of the suture anchor is performed with the pointed end portion of the inserter completely withdrawn from the opening in the suture anchor.

* * * * *